US008829265B2

(12) United States Patent
Alvarez Casanueva et al.

(10) Patent No.: US 8,829,265 B2
(45) Date of Patent: Sep. 9, 2014

(54) MELON PLANTS

(75) Inventors: Jose Ignacio Alvarez Casanueva, El Ejido/Almeria (ES); Bruno Foncelle, Sarrians (FR); Jean Louis Marie Edouard Nicolet, Sarrians (FR); Johannes Elizabert Van Doorn, El Ejido/Almeria (ES); Marc Oliver Seros, Saint-Sauveur (FR)

(73) Assignee: Syngenta Participations AG, Basel (CH)

( * ) Notice: Subject to any disclaimer, the term of this patent is extended or adjusted under 35 U.S.C. 154(b) by 709 days.

(21) Appl. No.: 12/549,728

(22) Filed: Aug. 28, 2009

(65) Prior Publication Data
US 2010/0034952 A1 Feb. 11, 2010

Related U.S. Application Data

(62) Division of application No. 11/031,578, filed on Jan. 7, 2005, now abandoned.

(60) Provisional application No. 60/535,631, filed on Jan. 9, 2004.

(51) Int. Cl.
*A01H 1/00* (2006.01)
*A01H 1/04* (2006.01)
*A23L 1/212* (2006.01)
*C12N 15/82* (2006.01)
*A01H 5/08* (2006.01)

(52) U.S. Cl.
CPC . *A23L 1/212* (2013.01); *A01H 1/04* (2013.01); *C12N 15/8245* (2013.01); *A01H 5/08* (2013.01)
USPC ........................................................ 800/267

(58) Field of Classification Search
USPC ................................. 800/309, 308
See application file for complete search history.

(56) References Cited

U.S. PATENT DOCUMENTS

| 5,354,946 | A | | 10/1994 | Dreyer et al. | |
|---|---|---|---|---|---|
| 5,476,998 | A | * | 12/1995 | Kataoka et al. | 800/262 |
| 6,420,631 | B1 | | 7/2002 | Copes | |
| 2003/0177539 | A1 | | 9/2003 | Copes | |

FOREIGN PATENT DOCUMENTS

| WO | WO 97/42333 | 11/1997 |
|---|---|---|
| WO | WO 00/32789 | 6/2000 |

OTHER PUBLICATIONS

Beaulieu et al (2003, J. Amer. Soc. Hort. Sci. 128:531-536).*
Ventura et al (1999, J. Hort. Sci. Biotechnol. 74:602-607).*
Burger et al (2003, J. Amer. Hort. Sci. 128:537-540).*
Stepansky et al., Genetic Resources and Crop Evol., 1999, 46, 53-62.
Ventura et al., J. Hort. Sci. Biotechnol., 1999, 74, 602-607.
Beaulieu et al., J. Amer. Soc. Hort. Sci., 2003, 128, 531-536.
Burger et al., J. Amer. Hort. Sci., 2003, 128, 537-540.
More et al., Genetic resources and breeding of muskmelon, Cucurbits Towards 2000. Proc. 6th Eucarpia meeting on Cucurbit Genetics and Breeding (Malaga, Spain, 1996), 120-127.
Seshadri et al., Cucurbits Towards 2000. Proc. 6th Eucarpia meeting on Cucurbit Genetics and Breeding (Malaga, Spain, 1996), 112-119.
Swarup et al., Genetic resources of Indian cucurbits, Cucurbits Towards 2000. Proc. 6th Eucarpia meeting on Cucurbit Genetics and Breeding (Malaga, Spain, 1996), 104-111.
Dr. Arthur A. Schaffer and Joseph Burger, Project Proposal Submitted to S&G Seeds, Dept. of Vegetable Crops, Volcani Center, dated Oct. 21, 1996, 2 pages total.
Brune et al., The Journal of Membrane Biology, 1998, 166, 197-203.
Burger et al., Journal of the American Society for Horticultural Science, Nov. 2002, 127, 6, 938-943.
Danin-Poleg et al., Euphytica, 2002, 125, 3, 373-384.
Danin-Poleg et al., Theoretical and Applied Genetics, 2001, 102, 61-72.
Dirlewanger et al., Theoretical and Applied Genetics, 1998, 97, 888-895.
Dirlewanger et al., Theoretical and Applied Genetics, 1999, 98, 18-31.
Etienne et al., Theoretical and Applied Genetics, 2002, 105, 145-159.
Etienne et al., Physiologica Plantarum, 2002, 114, 259-270.
Fang et al., Genome, 1997, 40, 841-849.
Fridman et al., Plant Physiology, Feb. 2003, 131, 603-609.
Gao et al., Plant Physiology, Mar. 1999, 119, 979-987.
Handley et al., Plant Physiology, 1983, 72, 497-502.
Ho, Annual Review of Plant Physiology and Plant Molecular Biology, 1988, 39, 355-378.
Ibrahim et al., HortScience, 1992, 27, 276-277.
Kubicki, Genetica Polonica, 1962, 3, 3, 265-274.
Lamikanra et al., Journal of Agricultural and Food Chemistry, Dec. 2000, 48, 12, 5955-5961.
Leach et al., Acta Horticulturae, 1989, 247, 353-358.
Maliepaard et al., Theoretical and Applied Genetics, 1998, 97, 60-73.
Mallick et al., Scientia Horticulturae, 1986, 28, 251-261.
McFeeters et al., Journal of Food Science, 1982, 47, 1859-1861.
Monforte et al., Theoretical and Applied Genetics, 2004, 108, 750-758.
Muller et al., The Journal of Membrane Biology, 2002, 185, 185-220.
Perin et al., Plant Physiology, May 2002, 129, 1-10.
Pitrat et al., Acta Hort. (ISHS), 2000, 510, 29-36.
Pitrat et al., Cucurbit Genetics Cooperative Report, 1998, 21, 69-81.
Purac Focus: Flavors and Acidulants, [online], [Published Dec. 2001] Retrieved from the Internet <URL: http://purac.nl/documents/literature/FlavorEn.pdf.>.
Sadka et al., Physiologica Plantarum, 2000, 108, 255-262.

(Continued)

*Primary Examiner* — Anne Kubelik
(74) *Attorney, Agent, or Firm* — Myers Bigel Sibley & Sajovec, PA

(57) ABSTRACT

The present invention relates to novel plants, in particular to melon plants capable of producing fruits with a new pleasant taste and to seeds thereof. The present invention further relates to fruits of melon plants of the present invention, wherein such fruits have organic acid content, low pH and high sugar contents. The present invention further relates to methods of making and using plants and fruits disclosed herein.

1 Claim, No Drawings

(56) References Cited

OTHER PUBLICATIONS

Sadka et al., Plant Science, Sep. 8, 2000, 158, 173-181.
Schaffer et al., Proc. Cucurbitaceae (ISHS), 2000, 510, 449-454.
Schaffer et al., Phytochemistry, 1987, 26, 7, 1883-1887.
Stepansky et al., Plant Systematics and Evolution, 1999, 217, 3-4, 313-332.
Stepansky et al., Genetic Resources and Crop Evolution, Feb. 1999, 46, 1, 53-62.
Sturm et al., Plant Physiology, Sep. 1999, 121, 1-7.
Sweeney et al., Journal of the American Dietetic Association, 1970, 57, 432-435.
Ventura et al., Journal of Horticultural Science and Biotechnology, Sep. 1999, 74, 5, 602-607.
Wang et al., Journal of Agricultural and Food Chemistry, 1996, 44, 210-216.
Watkins, Fruit Quality and its Biological Basis, 2002, 180-224.
Wu et al., Preliminary Study on Acid Melon Breeding, Presented at the Cucurbitaceae 2002 Conference, Naples, Florida, Dec. 12, 2002.
Yang et al., Plant Cell Physiology, 1998, 39, 5, 533-539.
File history of U.S. Appl. No. 11/031,578.
"UNECE Standard FFV-23 Concerning the Marketing and Commercial Quality Control of Melons," United Nations, 2006 Edition, 7 pages.
Mullins et al., "Specialty Muskmelons," Virginia Polytechnic Institute and State University (2009) 2906- 1372 (2 pages).
Schultheis et al., "Screening Melons for Adaptability in North Carolina," Retrieved Date: Jun. 25, 2012, From URL: http://www.hort.purdue.edu/newcrop/ncnu02/v5-439.html (8 pages).
"Vegetable Cultivar Descriptions for North America, Melon, Lists 1-26 Combined," North Carolina State University, Cucurbit Breeding, Horticultural Science, Retrieved Date: Jul. 3, 2012, From URL: http://cuke.hort.ncsu.edu/cucurbit/wehner/vegcult/melon.html (20 pages).
Agblor at al., "Musk Melons—Cantalope—Post-Harvest Handling and Storage" *Department of Plant Sciences*, University of Saskatchewan Jun. 2001 (3 pp).
Burger et al., "A Single Recessive Gene for Sucrose Accumulation in *Cucumis melo* fruit" *J. Amer. Soc. Hort. Sci.* 127(6):938-973 (2002).
Burger et al., "Development of Sweet Melon (*Cucumis melo*) Genotypes Combining High Sucrose and Organic Acid Content" *J. Amer. Soc. Hort. Sci* 128(4):537-540 (2003).
CoSeteng et al., "Influence of Titratable Acidity and pH on Intensity of Sourness of Citric, Malic, Tartaric, Lactic and Acetic Acids Solutions and on the Overall Acceptability of Imitation Apple Juice" *Canadian Institute of Food Science and Technology* 22(1):46-51 (1989).
Distelfield A. (Feb. 2000); M.Sc. Thesis Submitted to the Faculty of Agricultural, Food and Environmental Quality Sciences; The Hebrew University of Jerusalem (Hebrew Language, 13 pp).
Distelfield A. (Feb. 2000); M.Sc. Thesis Submitted to the Faculty of Agricultural, Food and Environmental Quality Sciences; The Hebrew University of Jerusalem (Full English LanguageTranslation; 40 pp).

Doienc-Sturm et al., "Evaluating of Some Quality Parameters of Different Apricot Cultivars Using HPLC Method" *Acta Alimentaria* 28(4):297-309 (1999).
Notice of Opposition #1 filed in the European Patent Office in corresponding European Patent No. 1587933 on May 12, 2009 (25 pp).
Notice of Opposition #2 filed in the European Patent Office in corresponding European Patent No. 1587933 on May 13, 2009 (16 pp).
Decision Minutes in the European Patent Office in corresponding European Patent No. 1587933 on Feb. 16, 2011 (8 pp).
Hartwig et al., "Flavor Characteristics of Lactic, Malic, Citric, and Acetic Acids at Various pH Levels" *Journal of Food Science* 60(2):384-388 (1995).
Khanom et al., "Relationship between Volatiles and Other Factors Indicating Quality of Melon (*Cucumis Meio* L. cv. Prince Melon) during Fruit Development and Storage" *Sci. Rep. Grag. Sch. Agric. & Biol. Sci.*, Osaka Pref. Univ. 55:7-14 (2003).
Letter from Opponent with Annex with Translation of Distelfeld (D1) Thesis submitted in corresponding European Patent No. 1587933 on Oct. 29, 2009 (16 pp).
Letter from Opponent in corresponding European Patent No. 1587933 on Dec. 29, 2010 (4 pp).
Lobit et al., "Modelling citrate metabolism in fruits: responses to growth and temperature" *Journal of Experimental Botany* 54(392):2489-2501 (2003).
Opposition Decision in the European Patent Office in corresponding European Patent No. 1587933 on Mar. 10, 2011 (77 pp).
Opposition Minutes in the European Patent Office in corresponding European Patent No. 1587933 on Apr. 19, 2011 (5 pp).
Opposition Terminated Decision to Maintain Patent in the European Patent Office in corresponding European Patent No. 1587933 on Jan. 25, 2012 (13 pp).
Patentee Response to Notice of Opposition in the European Patent Office in corresponding European Patent No. 1587933 on Jan. 4, 2010 including listed referenced cited in the opposition (36 pp).
Patentee Response to Summons to Attend Oral Proceedings in the European Patent Office in corresponding European Patent No. 1587933 on Dec. 29, 2010 (21 pp).
Renaud et al., "Melons: The Dessert of the Garden" *Seeds of Change* eNewsletter 42 Jul. 2004 (4 pp).
Rubico et al., "Sensory evaluation of acids by free-choice profiling" *Chemical Senses* 17(3):273-289 (1992).
Sortwell et al., "Improving the Flavor of Fruit Products with Acidulants" *Bartek Ingredients, Inc.*, Expotecnoalimentaria, Mar. 28, 1996 (10 pp).
Summons to Attend Oral Proceedings in the European Patent Office in corresponding European Patent No. 1587933 on Oct. 14, 2010 (16 pp).
The American HeritageThe American Heritage® Dictionary of the English Language: Fourth Edition: "Malic Acid" 2000 (1 p).
Withdrawal of Opposition by De Ruiter Seeds R&D B.V. in the European Patent Office in corresponding European Patent No. 1587933 on Apr. 29, 2010 (2 pp).

\* cited by examiner

MELON PLANTS

CROSS-REFERENCE TO RELATED APPLICATIONS

This application is a divisional of U.S. application Ser. No. 11/031,578, filed Jan. 7, 2005, which claims the benefit of U.S. Provisional Application No. 60/535,631, filed Jan. 9, 2004. The above applications are incorporated herein by reference in their entireties.

FIELD OF THE INVENTION

The present invention relates to novel plants, in particular to melon plants capable of producing fruits with a new pleasant taste. In particular, the fruits of the melon plants of the present invention have altered organic acid contents, lower pH when compared to current commercial sweet melon fruits, and high sugar contents.

BACKGROUND OF THE INVENTION

Melon (Cucumis melo L.) is a commercial crop grown worldwide. Cucumis melo is a member of the family Cucurbitaceae. The Cucurbitaceae comprises about 90 genera and 700 to 760 species, mostly of the tropics. The family includes pumpkins, squashes, gourds, watermelon, loofah and several weeds. Cucumis melo L. includes a very wide variety of cultivars producing fruits of different shape, external appearance and flesh color. Commercial melons generally produce sweet fruits known for example as Charentais, cantaloupe, honeydew, amarello, Piel de sapo, Kirkagak, Hamy, Ananas, Galia, Oriental that are usually consumed as dessert fruits. Cucumis melo L. also includes non-sweet, commercial cultivars consumed in the Middle to Far East in salad, cooking or pickling, as for example Alficoz, Faqqous, Chito, Conomon (Pitrat et al (2000) Eucarpia meeting Proceedings: 29-36). The taste and aroma of melon fruits is determined by a number of factors, including sugars, aroma volatiles, free amino acids, organic acids, pH and soluble minerals (Wang et al. (1996) J. Agric. Food Chem. 44: 210-216). Among the four primary tastes (sweet, sour, bitter, salty), sweetness is considered to be a very important component of good tasting melon fruits. In commercial melon fruits the sweet taste mostly results from high levels of sucrose (Burger et al. (2002) J. Amer. Soc. Hort. Sci. 127(6): 938-943). Sucrose is accumulated at the end of fruit development, during ripening process (Shaffer et al (1987) Phytochemistry 26: 1883-1887). Melon fruits also initially accumulate hexoses, mainly fructose and glucose, which are the dominant reducing sugars (Stepanski et al (1999) Genetic Resources and Crop Evolution 46: 53-62). An important taste component in melon fruits is sweetness, which is mainly the result of sugars accumulation. Sweetness correlates not only with the total sugars content, but also with the type of sugars. For example, 1 gram of glucose is the sweet equivalent of 0.7 gram of sucrose; 1 gram of fructose is the sweet equivalent of 1.7 gram of sucrose; 1 gram of inverted sugar, i.e. glucose plus fructose generated from 1 gram of sucrose, is the sweet equivalent of 1.3 gram of sucrose (J. A. BABOR et J. IBARZ (1935) Quimica General Moderna).

The flesh of sweet melon fruits has a pH usually above 6.0, but melon accessions are also known to have a much lower pH, as low as below 5.0. This low pH is widespread over many different melon types as for example Faqqous, Chito, Conomon, Momordica, Agrestis (Stepanski et al). In most of these cases, these melon types combine low pH and low sugar content, e.g. sucrose (Stepanski et al). These fruits are generally not edible in fresh consumption without dressing or cooking and, in some cases, they are even bitter. In most of these melon accessions with low pH, the mesocarp, which is the edible part of the fruit, represents a minor part of the total fruit, while the seed cavity and placenta represent a major part of the total fruit fresh weight. This is in contrast to sweet dessert melons, where the mesocarp represents a major part of the fruit. Also, in many cases, the fruit size or weight of the melon having low pH is below commercially acceptable ranges.

The fruit flesh of some melons has a sour taste (Kubicki (1962) Genetica Polonica 3:265-274). The cause for the sour taste remains unclear, but it has been linked with low pH in the fruit flesh (U.S. Pat. No. 5,476,998 and Danin-Poleg et al. (2002) Euphytica 125: 373-384). Single genes for sour taste (So) and pH have also been reported, although their genetic association is not clear (Danin-Poleg et al.).

Attempts have been made to produce melon fruits combining sour and sweet tastes. For example, Najd melons based on Arabic wild varieties have been reported (Ibrahim and Al-Zeir (1992) HortScience 27: 276-277). U.S. Pat. No. 5,476, 998 also described melons with a sour taste, with a mean pH value of 4.8 and a total soluble content of about 11. The melons in U.S. Pat. No. 5,476,998 are derived from MR-1, also known as PI124111 (Thomas, Eucarpia '92 pp 142), which is a C. melo Var. Momordica (Roxburg). Fruits of this melon showed low pH (Danin-Poleg et al.). This melon variety also involves poor fruit traits such as very mealy, non-aromatic and non-sweet flesh, very climacteric behavior and thin skin bursting at ripening. These undesired traits are difficult to remove by breeding and it is therefore expected that the development of commercial products from such a variety would be lengthy and difficult. Accordingly, there is an unmet need for melons producing fruits with alternative or improved tastes. In particular, there is an unmet need for melon fruits having new combinations of organoleptic characteristics and aroma.

SUMMARY OF THE INVENTION

The instant invention addresses the need for melon fruits with alternative or improved tastes. Accordingly, the instant invention discloses melon plants capable of producing fruits with novel combinations of organic acid contents and compositions, pH, and sugars contents and compositions. The invention also discloses methods of making and methods of using plants of the present invention and their fruits.

The inventors of the instant application have identified that there is a wide variability in the contents and composition of organic acids in melon fruits. In particular, the inventors of the present invention have identified that melon plants produce fruits with varying contents of citric acid and varying ratios of citric acid to malic acid. Accordingly, the inventors of the present invention have combined appropriate content of organic acids, low pH and desired sugar contents in a melon fruit to obtain novel and extremely pleasant tastes.

Accordingly, in one embodiment, the instant invention discloses melon plants capable of producing fruit with low pH and desired combinations of citric and malic acid contents, while maintaining or increasing levels of sugars currently observed in sweet melons. In one embodiment, the instant invention discloses melon plants capable of producing fruit with low pH and desired combinations of citric and malic acid contents, combined with desired combinations of sucrose and hexoses contents. In one embodiment, the present invention provides melon plants capable of producing fruits with elevated contents of citric acid and lower pH, when compared to current commercial melons. In one embodiment, melon plants of the present invention are obtained by introducing a low pH trait in a melon plant not comprising said trait. In one embodiment, melon plants of the present invention are obtained by introducing a low pH gene in a melon plant not comprising said gene. In one embodiment, the low pH gene is obtainable from line IND-35, deposited with NCIMB under Accession number NCIMB 41202. Accordingly, the present invention discloses melon plants comprising a low pH trait, and producing fruit comprising desired contents and compositions of organic acids, pH and contents and compositions of sugars. In one embodiment, increased citric acid contents are achieved while maintaining low levels of malic acid in the fruit. In one embodiment, fruits of melon plant of the instant invention have high ratios of citric acid to malic acid.

In one embodiment, the melon plants of the instant invention are capable of producing fruit with citric acid content equal or higher than about 400 mg per 100 g fresh weight (fwt). In one embodiment, melon plants of the instant invention are capable of producing fruit with a pH of about 4.2 to about 5.6. In one embodiment, melon plants of the instant invention are capable of producing fruit with a sugar content equal or higher than about 5.0 g per 100 g fwt. In one embodiment, melon plants of the instant invention are capable of producing fruit with a sugar content equal or higher than about 7.0 g per 100 g fwt.

In one embodiment, the present invention discloses melon plants capable of producing fruit with citric acid content equal or higher than about 400 mg per 100 g fwt, pH of about 4.2 to about 5.6, and sugar content equal or higher than about 5.0 g per 100 g fwt.

In one embodiment, the present invention discloses a *C. melo* plant capable of producing a fruit comprising at maturity:
  a) about 400 mg to about 1,200 mg citric acid per 100 g fwt;
  b) pH of about 4.2 to about 5.6; and
  c) about 5.0 g to about 15.0 g sugar per 100 g fwt.

In one embodiment, the citric acid content of a fruit of a plant according to the present invention is about 400 mg to about 1,000 mg citric acid per 100 g fwt. In one embodiment, melon plants of the present invention produce edible fruits, preferably with a round or oval shape, and preferably weighting over 450 grams. The flesh of the melons of the present invention is preferably green, yellow, white or orange.

In one embodiment, the instant invention discloses melon plants capable of producing a very sweet juicy fruit with tart-refreshing sour taste, and referred herein to as "Citric+" plants or fruits. Such fruits comprise high contents of citric acid and low pH, increasing the acid taste and providing a tart perception, which covers still too flat and poor flavors of early mature fruits.

In one embodiment, a fruit of a Citric+plant of the present invention at maturity comprises:
  a) about 600 to about 1,200 mg citric acid per 100 g fwt;
  b) pH of about 4.2 to about 5.1; and
  c) about 5.0 g to about 15.0 g sugar per 100 g fwt.

In one embodiment, the citric acid content of a fruit of a plant according to the present invention is about 600 mg to about 1,000 mg citric acid per 100 g fwt.

In one embodiment, the present invention discloses a melon plant capable of producing a sweet aromatic fruit with mild-fruity sour taste, referred herein as "Citric-" melon plant or fruit. Such fruits comprise relatively high contents of citric acid and mildly low pH. This mild low pH makes a fruity sour perception, which covers other still too flat and poor flavors of early mature fruits.

In one embodiment, the fruit of a Citric-plant of the present invention at maturity comprises:
  a) about 400 to about 650 mg citric acid per 100 g fwt;
  b) pH of about 4.6 to about 5.6; and
  c) about 5.0 g to about 15.0 g sugar per 100 g fwt.

In one embodiment, the present invention discloses a melon plant capable of producing fruit with low pH and a flesh of deep orange color. In one embodiment, the present invention discloses a *C. melo* plant capable of producing fruit with pH of about 4.5 to about 5.6, wherein said fruit has orange flesh rated 4 or higher.

In one embodiment, characteristics of melon fruits described herein are measured on fruits of melon plants grown in open fields or in plastic houses, and harvested at maturity. In one embodiment fruits are harvested from early maturity to late maturity (stages 2-4, as described herein). In one embodiment, a fruit of the present invention is at maturity when its sucrose contents is at or over 2 g sucrose per 100 g fwt.

In one embodiment, the present invention discloses a *C. melo* plant capable of producing fruit comprising an acid savor of about 1.6 to about 3.8 and a sugar savor of about 4.3 to about 5.8. In one embodiment, the present invention discloses a *C. melo* plant capable of producing fruit comprising an acid savor of about 2.5 to about 3.8 and a sugar savor of about 4.3 to about 5.6. In one embodiment, the present invention discloses a *C. melo* plant capable of producing fruit comprising an acid savor of about 1.6 to about 3.0 and a sugar savor of about 5.2 to about 5.8. In one embodiment, the acid savor and sugar savor are determined by an Expert panel, for example as described in Example 12 herein. In one embodiment, such fruit comprises a pH and citric acid content as described herein. In one embodiment, such fruit comprises a pH, organic acid contents and compositions and sugar contents and compositions as described herein.

In one embodiment, the present invention discloses a *C. melo* plant comprising a DNA sequence, which co-segregates with a low pH trait. In one embodiment, the DNA sequence is a template for amplification of a DNA fragment described herein using the primers described herein. In one embodiment, the present invention discloses such primers and DNA fragments amplified using these primers. In one embodiment, a DNA fragment described herein is amplified from DNA of said plant using the primers described herein. The DNA fragments are used as molecular markers for a low pH trait. In one embodiment, a DNA fragment of about 168 bp to about 178 bp is amplified from the DNA of said plant when the primers capable of identifying the CMAT141 marker are used. In one embodiment, a DNA fragment of 168 bp, 173 bp, 169 bp, 172 bp or 178 bp is amplified when the primers capable of identifying the CMAT141 marker are used. In one embodiment, a DNA fragment of less than 176 bp is amplified when the primers capable of identifying the CMAT141 marker are used. In one embodiment, a DNA fragment of less than 175 bp is amplified when the primers capable of identifying the CMAT141 marker are used. In one embodiment, a DNA fragment of about 218 bp to about 253 bp is amplified when the primers capable of identifying the NE0585 marker are used. In one embodiment, a DNA fragment of 230 bp, 232 bp, 218 bp, 229 bp, 234 bp or 239 bp is amplified when the primers capable of identifying the NE0585 marker are used. In one embodiment, a DNA fragment of about 121 bp to about 145 bp is amplified when the primers capable of identifying the NE1746 marker are used. In one embodiment, a DNA fragment of 124 bp, 127 bp, 133 bp, 142 bp or 145 bp is amplified when the primers capable of identifying the NE1746 marker are used.

In one embodiment, the present invention discloses a *C. melo* plant comprising a DNA sequence, which is a template for amplification of a DNA fragment indicative for the presence of a low pH trait in said plant (acid fragment) or for the absence of the low pH trait (basic fragment) in said plant. In one embodiment, the present invention discloses a *C. melo* plant comprising a DNA sequence, which is a template for amplification of a basic fragment linked to a low pH trait, wherein said DNA sequence is linked to said low pH trait. In one embodiment, the *C. melo* plant comprises such a DNA sequence on one side of a low pH gene. In one embodiment, the *C. melo* plant comprises such a DNA sequence on both sides of a low pH gene. In one embodiment, a fruit of such a plant comprise a pH within the ranges disclosed herein. In one embodiment, fruits of such a plant comprise the contents and compositions of sugars as described herein. In one embodiment, fruits of such a plant comprise the contents and compositions of organic acids as described herein. In one embodiment, fruits of such a plant comprise the pH, contents and compositions of sugars and contents and compositions of organic acids as described herein.

In one embodiment, the characteristics of a fruit according to the present invention described herein remain stable after the fruit reaches maturity. In one embodiment, such characteristics remain stable after a fruit reaches maturity when the fruit is kept on the plant. In one embodiment, such characteristics remain stable when the fruit is harvested and kept in storage after harvest. This allows for a reduced harvest frequency, and to store or ship a fruit of the present invention without loosing its organoleptic characteristics and aroma. In one embodiment, the pH of a fruit of the instant invention remains stable after a fruit reaches maturity. In one embodiment, the citric acid content of a fruit of the present invention remains stable after a fruit reaches maturity. In one embodiment, the malic acid content of a fruit of the present invention remains stable after a fruit reaches maturity. In one embodiment, the ratio citric acid to malic acid of a fruit of the present invention remains stable after a fruit reaches maturity. In one embodiment, the pH and organic acid contents and composition of a fruit of the present invention remain stable after a fruit reaches maturity. In one embodiment, such characteristics remain within the ranges described herein after a fruit reaches maturity. In one embodiment, the present invention discloses a plant capable of producing a fruit, the characteristics of which remain stable for at least 2 days when the fruit is kept on the plant, in one embodiment for at least 3 days when the fruit is kept on the plant, in one embodiment for at least 4 days when the fruit is kept on the plant. In one embodiment, the present invention discloses a plant capable of producing a fruit, the characteristics of which remain stable for at least 5 days when kept in storage at 20° C., in one embodiment for at least 7 days when kept in storage at 20° C., in one embodiment for at least 9 days when kept in storage at 20° C. In one embodiment, the present invention discloses a plant capable of producing a fruit, the characteristics of which remain stable for at least 7 days when kept in storage at 8-12° C. followed by at least 2 days at 20° C., in one embodiment for at least 12 days when kept in storage at 8-12° C. followed by at least 2 days at 20° C., in one embodiment for at least 26 days when kept in storage at 8-12° C. followed by at least 2 days at 20° C. In one embodiment, a plant of the instant invention is capable of producing a long shelf-life fruit (LSL) or a medium shelf-life fruit (MSL). In one embodiment, a plant of the instant invention is capable of producing a non-turning fruit or low turning fruit. In one embodiment, a plant of the instant invention is capable of producing a non-climacteric fruit or a low climacteric fruit.

The instant invention further discloses seeds of a *C. melo* plant of the present invention, and seeds of the progeny thereof, wherein said progeny seed is capable of producing a plant of the present invention. The instant invention further discloses parts of a *C. melo* plant of the present invention, e.g. ovules or pollen, and fruits of a *C. melo* plant of the present invention. The instant invention further discloses the flesh of a fruit of a *C. melo* plant of the present invention. The instant invention further discloses the juice of a fruit of a *C. melo* plant of the present invention.

The present invention further discloses the use of the flesh of a fruit according to the present invention in a fresh cut product. The present invention further discloses the use of the juice of a fruit according to the present invention in a soft drink.

The present invention further discloses methods of increasing the citric acid content of a plant comprising obtaining a first *C. melo* plant; crossing said first *C. melo* plant with a second *C. melo* plant comprising a low pH trait, obtaining a progeny *C. melo* plant, determining the pH and citric acid content of a fruit of said progeny plant, selecting a fruit of said progeny *C. melo* plant which has increased citric acid content, when compared to a fruit of said first *C. melo* plant. In one embodiment, said progeny *C. melo* plant has a lower pH, when compared to a fruit of said first *C. melo* plant. In one embodiment, the method comprises detecting a DNA fragment described herein using the primers described herein. The present invention further discloses the use of a melon plant comprising a low pH trait to obtain a melon plant of the present invention. In one embodiment, the melon plant comprising a low pH trait further has the ability of accumulating relevant levels of sugars, for example sucrose. In one embodiment, the melon plant comprising a low pH accumulates high levels of citric acid. In one embodiment, the melon plant comprising a low pH accumulates low levels of malic acid. In one embodiment, the melon plant comprising a low pH trait further has the ability of accumulating relevant levels of sugars, for example sucrose and of accumulating high levels of citric acid and of accumulating low levels of malic acid. In one embodiment, the melon plant comprising a low pH is a plant of line IND-35 or a descendent thereof.

The present invention further discloses a method to produce seed of a plant according to the instant invention comprising obtaining a plant of the present invention, self-pollinating said plant or crossing said plant with another melon plant, and harvesting progeny seed. The present invention further discloses a method to vegetatively propagate a melon plant according to the present invention. The present invention further discloses a method for producing a fruit comprising planting a plant according to the present invention, growing said plant and harvesting a fruit, wherein said fruit comprises the characteristics described herein. The method further comprises storing said fruit, for example as described herein. The method further comprises shipping said fruit. In one embodiment, the characteristics of said fruit described herein remain stable during the storage of said fruit. In one embodiment, the characteristics of said fruit described herein remain stable during the storage of said fruit. In one embodiment, a plant of the present invention is an inbred line, a hybrid, a dihaploid, or a vegetatively propagated clone.

The present invention thus provides melon fruits offering a pleasant acid component but avoiding an astringent taste. This enhances or complements melon flavors to their maximum potential. These combinations of organic acid content and low pH with high sugars provide new ranges and classes of appealing tastes for fresh consumption or the fresh cut or fresh juice industry. Low pH in fruit flesh also prevents bacterial contamination in fresh cut and juice industrial processes.

DEFINITIONS

Trait: characteristic or phenotype. For example, in the context of the present invention a low pH trait confers a low pH, for example from about 4.2 to about 5.6, to the flesh of a melon fruit. A trait may be inherited in a dominant or recessive manner, or in a partial or incomplete-dominant manner. A trait may be monogenic or polygenic, or may also result from the interaction of one or more genes with the environment.

Monogenic: determined by a single locus.

Polygenic: determined by more than one locus.

Dominant: results in a complete phenotypic manifestation at heterozygous or homozygous state.

Recessive: manifests itself only when present at homozygous state.

Partial or incomplete-dominance: when present at the heterozygous stage determines a phenotype that is intermediate to that of the homozygous stage or when the trait is absent.

Backcrossing: backcrossing is a process in which a hybrid progeny is repeatedly crossed back to one of the parents.

Locus: region on a chromosome, which comprises a gene contributing to a trait.

Genetic linkage: association of characters in inheritance due to location of genes in proximity on the same chromosome. Measured by percent recombination between loci (centi-Morgan, cM).

Quantitative Trait Loci (QTL): Quantitative trait loci (QTL) refer to genetic loci that control to some degree numerically representable traits that are usually continuously distributed.

Isogenic: plants, which are genetically identical, except that they may differ by the presence or absence of a gene, a locus conferring a trait or heterologous DNA sequence.

Marker assisted selection: refers to the process of selecting a desired trait or desired traits in a plant or plants by detecting one or more nucleic acids from the plant, where the nucleic acid is associated with the desired trait.

Dihaploid: doubling of haploid (single chromosome) status of the genome (e.g. through another culture or microspore culture) giving a complete homozygous plant.

"Tester" plant: plant used to characterize genetically a trait in a plant to be tested. Typically, the plant to be tested is crossed with a "tester" plant and the segregation ratio of the trait in the progeny of the cross is scored.

Gene: Unit of inheritance. Genes are located at fixed loci in chromosomes and can exist in a series of alternative forms called alleles.

Allele: One of a pair or series of forms of a gene, which are alternative in inheritance because they are situated at the same locus in homologous chromosomes.

Homozygous: Having like alleles at one or more corresponding loci on homologous chromosomes.

Heterozygous: Having unlike alleles at one or more corresponding loci on homologous chromosomes.

Low pH gene: gene, which when present in the genome of a plant leads to a lower pH of the flesh of a fruit of said plant, when compared to a plant not comprising said gene.

Low pH melon plant: melon plant comprising a low pH trait. In one embodiment, the pH of a fruit of a low pH melon plant is from about 4.2 to about 5.6.

*Cucumis melo* L: also referred herein to as *C. melo* or melon.

Cavity: refers to the center of the melon fruit containing seeds and maternal tissues.

Soluble Solids: refers to the percent of solid material found in the fruit tissue, the vast majority of which is sugars.

Climacteric/non-climacteric: as for example defined in Watkins (2002) "Ethylene synthesis, mode of action, consequences and control" In: Michael Knee (ed) "Fruit Quality and its Biological Basis". Sheffield Academic Press, Sheffield, UK. Chapter 8 pp. 180-224, in particular at page 181, section 8.2.1, first two paragraphs.

Turning melon: turning refers to the marked change in rind color of a melon fruit when it reaches maturity, for example from green to yellow rind in Galia types, or from gray to creamy-yellow rind in Charentais types. This change of color is related to the degradation of green pigments occurring when the fruit reaches maturity.

Non-turning/low-turning melon: the rind color of a fruit of a non-turning or low turning melon does not dramatically change upon maturation. In the rind of the fruit of non-turning or low turning melon, there may be a continuous slight increase in yellow component in the stable background of the rind, as for example in Piel de Sapo type or in honeydew types. In low-turning melons, a slight pigment degradation may also be observed in connection with senescence of the fruit rather than with reaching maturity, which occurs earlier.

DETAILED DESCRIPTION OF THE INVENTION

The present invention provides *C. melo* plants capable of producing fruits with novel tastes. In particular, the present invention provides melon plants capable of producing fruits with novel combinations of organic acid contents, pH and sugar contents. The inventors of the instant application have identified that melon fruits contain various levels of organic acid, e.g. citric acid. The inventors of the instant application also have identified that melon fruits contain various relative contents citric acid and malic acid. Moreover, the inventors of the instant application have determined that by introducing a low pH trait into a sweet melon background, a reduction in pH and an increase in the citric acid content in the fruit are obtained, further expanding the ability to manipulate the taste of a melon fruit. In one embodiment, melon fruits of the present invention have low contents of malic acid. Accordingly, the present invention discloses melon plants producing fruits having elevated citric acid contents and lower pH, as described herein. In one embodiment, sugar levels observed in fruits of plants of the instant invention are maintained at levels present in currently available sweet melons or increased. Accordingly, plants of the present invention are capable of producing fruits with novel, pleasant tastes. Measurements of pH, citric acid and malic acid contents, and sugar contents described herein were carried out are shown in Examples 1 to 5. Tables 1A and 1B herein disclose representative melon plants according to the present invention and their fruits.

In one embodiment, the melon plants of the instant invention are capable of producing fruit with citric acid content equal or higher than about 400 mg per 100 g fresh weight (fwt). In one embodiment, melon plants of the instant invention are capable of producing fruit with a pH of about 4.2 to about 5.6. In one embodiment, melon plants of the instant invention are capable of producing fruit with a sugar content equal or higher that about 5.0 g per 100 g fwt. In one embodiment, the present invention discloses melon plants capable of producing fruit with citric acid content equal or higher than about 400 mg per 100 g fwt, pH of about 4.2 to about 5.6, and sugar content equal or higher that about 5.0 g per 100 g fwt.

In one embodiment, the present invention discloses a *C. melo* plant capable of producing a fruit comprising at maturity:
 a) about 400 mg to about 1,200 mg citric acid per 100 g fwt;
 b) pH of about 4.2 to about 5.6; and
 c) about 5.0 g to about 15.0 g sugar per 100 g fwt.

In one embodiment, the fruit comprises about 400 mg to about 1,000 mg citric acid per 100 g fwt. In one embodiment, the fruit comprises about 450 mg to about 950 mg citric acid per 100 g fwt, in one embodiment about 475 mg to about 900 mg citric acid per 100 g fwt. In one embodiment, the fruit has a pH of about 4.3 to about 5.4, in one embodiment about 4.4 to about 5.1. In one embodiment, the fruit comprises about 5.5 g to about 13.0 g sugar per 100 g fwt. In one embodiment, the fruit comprises about 7.0 g to about 15.0 g sugar per 100 g fwt.

In one embodiment, the ratio citric acid to malic acid in a fruit of said plant is greater than 4.4, in one embodiment greater than 5, in one embodiment greater than 10. In one embodiment, the ratio citric acid to malic acid in a fruit of said plant is less than 450, in one embodiment less than 200, in one embodiment less than 150. In one embodiment, a fruit of said plant comprises less than about 85 mg malic acid per 100 g fwt, in one embodiment less than about 75 mg malic acid per 100 g fwt.

In one embodiment, the ratio sucrose to hexoses in a fruit of said plant is about 1:1, in one embodiment between about 1:1 and about 1:2, in one embodiment between about 1:1 and about 2:1.

In one embodiment, the flesh of a fruit of said plant is orange, white, green or yellow. In one embodiment, said fruit is edible in fresh consumption. In one embodiment, the mesocarp of a fruit of said plant represents more than 50% of the total fresh fruit weight.

In one embodiment, the *C. melo* plant comprises a low pH trait. In one embodiment, the low pH trait is obtainable from a plant of line IND-35, representative seeds of which is deposited under Accession number NCIMB 41202, or a descendent of said line IND-35. In one embodiment, the low pH trait is homozygous or heterozygous in said plant.

In one embodiment of the instant invention, melon plants referred to as "Citric+" plants are disclosed. Such plants are capable of producing a very sweet juicy fruit with tart-refreshing sour taste. Such fruits comprise high contents of citric acid and low pH, increasing the acid taste and providing a tart perception. This is compensated by a high sugar content, in one embodiment by elevated levels of reducing sugars (glucose and fructose). The high reducing sugar content is particularly pronounced in early mature stages. The combination of tart and sweet tastes, which cannot be obtained by currently available sweet melon, is appreciated by consumers. The tart-refreshing sour sweet melon combination satisfies this need. This fruity tart perception also cover still too flat and poor flavors of early mature fruits. In one embodiment, Citric+plants are generally obtained by introducing a low pH trait, for example from line IND-35, into an oriental melon background. In one embodiment, the oriental melon background is selected for one or more of the following criteria: high citric acid content, low malic acid content, high citric acid to malic acid content, high sugar content, high hexose content, high ratio hexoses to sucrose, high juiciness. During the introduction of the low pH trait, careful selection for the above characteristics is maintained until a desired progeny is obtained.

For example, Examples 9, 10 and 11 describe the construction of such plants. Alternative *C. melo* plants can also be screened for desired characteristics and are used as starting materials as described herein.

In one embodiment, a fruit of a Citric+plant of the present invention at maturity comprises:
 a) about 600 to about 1,200 mg citric acid per 100 g fwt;
 b) pH of about 4.2 to about 5.1; and
 c) about 5.0 g to about 15.0 g sugar per 100 g fwt.

In one embodiment, the fruit comprises about 600 to about 1,000 mg citric acid per 100 g fwt. In one embodiment, the fruit comprises about 650 to about 950 mg citric acid per 100 g fwt.

In one embodiment, the pH of the fruit is about 4.4 to about 5.0.

In one embodiment, said fruit comprises about 7.0 g to about 13.0 g sugar per 100 g fwt. In one embodiment, the ratio citric acid to malic acid in a fruit of said plant is greater than 6, in one embodiment greater than 7, in one embodiment greater than 10. In one embodiment, the ratio citric acid to malic acid in a fruit of said plant is less than 450, in one embodiment less than 200. In one embodiment, a fruit of said plant comprising less than about 85 mg malic acid per 100 g fwt, in one embodiment less than about 75 mg malic acid per 100 g fwt, in one embodiment less than about 60 mg malic acid per 100 g fwt.

In one embodiment, a fruit of a plant of the present invention has a green or white flesh and at maturity comprises:
 a) about 600 to about 1,200 mg citric acid per 100 g fwt;
 b) pH of about 4.2 to about 5.1; and
 c) about 5.0 g to about 15.0 g sugar per 100 g fwt.

In one embodiment, the fruit comprises about 600 to about 1,000 mg citric acid per 100 g fwt. In one embodiment, said fruit with green or white flesh comprises at maturity about 8.0 g to about 12.0 g sugar per 100 g fwt. In one embodiment, said fruit with green or white flesh has at maturity a ratio citric acid to malic acid between about 25 and 200. In one embodiment the malic acid content of said fruit is less than about 50 mg malic acid per 100 g fwt, in one embodiment less than about 30 mg malic acid per 100 g fwt. In one embodiment, the ratio sucrose to hexoses in a fruit of said plant is about 1:1, in one embodiment between about 1:1 and about 2:1.

In one embodiment, a fruit of a plant of the present invention has orange flesh and comprises at maturity:
 a) about 600 mg to about 750 mg citric acid per 100 g fwt;
 b) pH of about 4.5 to about 5.1; and
 c) about 6.0 g to about 13.0 g sugar per 100 g fwt.

In one embodiment, the ratio citric acid to malic acid in said fruit is between about 4.4 and 30. In one embodiment, the fruit comprises about 7.0 g to about 13.0 g sugar per 100 g fwt.

In one embodiment, the present invention discloses a melon plant capable of producing a sweet aromatic fruit with mild-fruity sour taste, referred herein as "Citric-" melon plant or fruit. Such fruits comprise relatively high contents of citric acid and mildly low pH. This mild low pH makes a fruity sour perception that cover other still too flat and poor flavors of early mature fruits and without affecting the full expression of fruit flesh flavors and colors of further fully mature fruits. Further during ripening (early to late mature), fruits follow relevant increases of pH, decrease of acidity, in line with the weak buffer potential from the low citric acid content. This provides fully mature fruits with a very slight sour note to the full expression of very sweet and aromatic melon flavors. Melon flavor is based primarily on sweetness and aromas that usually get the full expression on really advanced fruit ripening stages. Early ripe melons are often described as unpleasant tasteless as sugars and aromas are below expectation and not any other component of flavor is present. In other fruits, such as strawberry, peach, or oranges, acid taste makes a well appreciated complement in this early ripe stages. The mild-fruity sour and sweet melon combination avoids or limits the tasteless risk on early ripe melons.

In one embodiment, Citric-plants are obtained by introducing a low pH trait, for example from line IND-35, into a Charentais melon background. In one embodiment, the Charentais melon background is selected for one or more of the following criteria: low citric acid content, low malic acid content, relatively high citric acid to malic acid content, high sugar content, high sucrose content. During the introduction of the low pH trait, careful selection for the above characteristics is maintained until a desired progeny is obtained.

For example, Example 11 describes the preparation of such plants. Alternative *C. melo* plants can also be screened for desired characteristics and can be used as starting materials as described herein.

In one embodiment, the fruit of a Citric-plant of the present invention at maturity comprises:

a) about 400 to about 650 mg citric acid per 100 g fwt;

b) pH of about 4.6 to about 5.6; and c) about 5.0 g to about 13.0 g sugar per 100 g fwt.

In one embodiment, the fruit comprises about 450 to about 600 mg citric acid per 100 g fwt.

In one embodiment, the fruit comprises a pH of about 4.8 to about 5.4, in one embodiment to about 5.2. In one embodiment, the fruit comprises about 5.0 g to about 13.0 g sugar per 100 g fwt, in one embodiment about 6.0 g to about 12.0 g sugar per 100 g fwt. In one embodiment, the fruit comprises about 7.0 g to about 13.0 g sugar per 100 g fwt.

In one embodiment, a fruit of a plant of the present invention has orange flesh and comprises at maturity:

a) about 400 mg to about 550 mg citric acid per 100 g fwt;

b) pH of about 4.8 to about 5.6; and c) about 5.0 g to about 11.0 g sugar per 100 g fwt.

In one embodiment, the ratio citric acid to malic acid in said fruit is between about 4.4 and 10. In one embodiment, the fruit comprises about 7.0 g to about 11.0 g sugar per 100 g fwt.

TABLE 1A

Summary of data for lines
Table 1A discloses representative lines of the present invention. The data shown in Table 1A are averages based on measurements from individual trials. The data for the individual trials are disclosed in Tables 9-13 in the Examples below.

| | LINES (averages) Plastic house data | | nr. frt | tot. sugar avg g/100 g | sucrose avg g/100 g | hexose avg g/100 g | hex/suc inv activity | pH avg | citric avg mg/100 g | citric/ malic | malic avg mg/100 g |
|---|---|---|---|---|---|---|---|---|---|---|---|
| Green Flesh | YUSOL | High pH | 34 | 9.85 | 4.50 | 5.34 | 1.1 | 6.05 | 265 | 24 | 11 |
| | YUSAZ A | Low pH, Citric− | 246 | 8.92 | 3.24 | 5.68 | 1.8 | 4.67 | 577 | 19 | 31 |
| | YUSAZ B | Low pH, Citric+ | 30 | 8.70 | 2.16 | 6.54 | 3.0 | 4.59 | 832 | 16 | 53 |
| White Flesh | SOLAZ/1 | Line | 71 | 6.97 | 2.16 | 4.81 | 2.2 | 4.59 | 579 | 23 | 25 |
| | SOLAZ/2 | Line | 43 | 6.19 | 1.92 | 4.27 | 2.2 | 4.64 | 590 | 47 | 13 |
| Orange Flesh | L53AZ A | Low pH, Citric− | 76 | 7.09 | 2.51 | 4.42 | 1.8 | 4.89 | 509 | 3 | 153 |
| | L53AZ B | Low pH, Citric+ | 52 | 8.11 | 4.24 | 3.87 | 0.9 | 4.81 | 701 | 10 | 67 |
| | L53 | High pH | 10 | 8.29 | 5.05 | 3.23 | 0.6 | 6.67 | 92 | 1 | 93 |

TABLE 1B

Summary of data for hybrids
Table 1B discloses representative hybrids of the present invention. The data shown in Table 1B are averages based on measurements from individual trials. The data for the individual trials are disclosed in Tables 9-13 in the Examples below. Mehari means the female parent of hybrid MEHARI.

| | HYBRIDS (average) Plastic house (PS) & Open Field (OP) data | | nr. frt | tot. sugar avg g/100 g | sucrose avg g/100 g | hexose avg g/100 g | hex/suc inv activity | pH avg | citric avg mg/100 g | citric/ malic | malic avg mg/100 g | |
|---|---|---|---|---|---|---|---|---|---|---|---|---|
| Green Flesh | YUSAZ A X YUSOL | Low pH, Citric+ | 17 | 9.70 | 4.46 | 5.24 | 1.2 | 4.77 | 692 | 46 | 15 | PS |
| | MILENIUM-DENEV F1 | High pH | 12 | 7.61 | 3.47 | 4.13 | 1.4 | 5.88 | 444 | X | 0 | OP |
| White Flesh | SOLAZ/1 X YUSOL | Solaz1 x Yusol | 26 | 9.71 | 6.40 | 3.31 | 0.5 | 4.75 | 760 | 58 | 13 | OP |
| | SOLAZ/2 X YUSOL | Solaz2 x Yusol | 13 | 9.08 | 6.26 | 2.82 | 0.5 | 4.70 | 782 | 162 | 6 | OP |
| | SOLAR F1 | High pH | 8 | 8.93 | 4.39 | 4.54 | 1.2 | 6.48 | 305 | 35 | 9 | PS |
| Orange Flesh | Mehari/L53AZ A | Low pH, Citric− | 13 | 7.34 | 2.24 | 5.10 | 2.3 | 4.98 | 487 | 6 | 78 | PS |
| | Mehari/L53AZ B | Low pH, Citric+ | 17 | 8.35 | 3.37 | 4.97 | 1.5 | 4.76 | 663 | 11 | 60 | OP |
| | Mehari/L53 | High pH | 14 | 8.80 | 3.96 | 4.84 | 1.2 | 6.31 | 274 | 5 | 54 | PS |

The instant invention demonstrates that the manipulation of the degree of sourness in a fruit produce valuable taste variations. Sourness is a result of the interaction between several parameters, pH being one of the most important ones along with organic acids contents and compositions. The pH greatly influences the degree of dissociation of acids involved in taste. Each acid has a different dissociation constant (pKa), which refers to the pH, at which 50% of the acid is dissociated in its relative ions and H+. A lower pH results in more of the acid that is not in dissociated form. The sourness perception comes mainly from the undissociated form of the acid. This explains why, at higher pH levels, weaker acids such as organic acids with a higher pKa are perceived as sourer than stronger acids.

The pH of a solution is correlated with the concentration and pKa of the acid. Equinormal solutions of stronger acids are sourer than weaker ones, since they have a much lower pH. The higher the concentration of the acid (titratable acidity), the more sour the acid will be perceived. Sourness is also correlated with the chemical structure of the acidulant, the number of carboxylic groups, the molecular weight, and polarity of the molecule (see e.g. PURAC Biochem, Gorinchen, The Netherlands, "Flavor Special", www. Purac.com). Besides sourness, each food acid has its own flavor characteristics in terms of lasting time, flavor intensity and the contribution to other non-sour flavor notes such as astringency, bitterness and sweetness.

The major organic acids in melon fruits are succinic acid, malic acid and citric acid (Wang et al. (1996) J. Agric. Food Chem. 44: 210-216). Malic acid tends to be associated either with very unripe phases or with senescence and degenerative phases of fruit over-ripening, and its dominance in the taste is generally not preferred. In the fruit flesh, gradients of increasing malic acid contents are observed from close to the seed cavity to close to the fruit rind. Citric acid has a lower pKa than malic acid. Citric acid has more tart and a clean effect, which often overpowers other taste or aromas notes. In contrast to malic acid, fruit flesh gradients of decreasing citric acid contents are observed from more ripe areas close to seed cavity to areas close to the fruit rind. Such a gradient is also observed for sugars.

Thus, in melon fruits of the instant invention, higher sugar contents and high citric acid contents tend to be associated in the fruit flesh to provide high contents of both in the most flavorful areas of the fruit, resulting in a very pleasant new taste.

Also, in the melon fruits of the instant invention, the sour perception is higher when the pH is low and the citric acid content high.

In one embodiment, fruits according to the instant invention were tested by an Expert panel of trained tasters. Sensory characteristics of the fruits were measured on a scale of quotation from 0 to 9. The pH, organic acid contents and sugar contents of the fruits were also measured. The results of the Expert panel are described in Example 12, Tables 14 and 15. The sensory analysis shows that the acid savor in fruits of the instant invention is a function of the pH and of the citric acid content in the fruit. Based on data gathered from mature and unripe fruits, the Expert panel determined the following formula for the correlation between the acid savor and pH and citric acid contents in a fruit: Acid savor=13, 12−(2.97× pH)+ (0,00587× citric acid content (mg/100 g fwt)), with r2=0.70.

Accordingly, in one embodiment, the present invention discloses a C. melo plant capable of producing fruit comprising an acid savor above about 0.5 as determined by an Expert panel. In one embodiment, the present invention discloses a C. melo plant capable of producing fruit comprising an acid savor of about 1.6 or above. In one embodiment, the present invention discloses a C. melo plant capable of producing fruit comprising an acid savor above about 0.5 and a sugar savor of about 4.3 or above. In one embodiment, the present invention discloses a C. melo plant capable of producing fruit comprising an acid savor of about 1.6 to about 3.8 and a sugar savor of about 4.3 to about 5.8.

In one embodiment, the present invention discloses a C. melo plant capable of producing fruit comprising an acid savor of about 2.5 to about 3.8 and a sugar savor of about 4.3 to about 5.6. Hybrids YUSOL X SOLAZ and Mehari X L53 AZ B are representative examples of such plant.

In one embodiment, such fruit comprises a pH and citric acid content as described herein. In one embodiment, the present invention discloses a C. melo plant capable of producing fruit comprising an acid savor of about 1.6 to about 3.0 and a sugar savor of about 5.2 to about 5.8. Hybrids YUSAZ X YUSOL, Mehari X L53 AZ A and TD X L53 AZ A are representative examples of such plant.

In one embodiment, such fruit comprises a pH and citric acid content as described herein. In one embodiment, such fruit comprises a pH, organic acid contents and compositions and sugar contents and compositions as described herein.

It is understood that values of Expert panels vary depending on the pH, citric acid content and sugar content of a fruit.

The inventors of the present invention have screened melon entries and accessions for the content in citric acid and sugars and compositions and have determined variations within C. melo types (see Table 2). For example, some Charentais-type melons were found to have low citric acid contents (for example Lunastar in Table 2). Some Charentais type fruits were also found to have a relatively low citric acid to malic acid ratio and a high ratio of sucrose to hexoses. On the other hand, Oriental-type melons, such as Japanese rocky types melon, were found to have higher contents in citric acid (for example YUCA in Table 2). A representative of YUCA has been deposited with NCIMB, Aberdeen, AB243RY, Scotland on Dec. 17, 2003 as YUC-15 under Accession number NCIMB 41203. These melons were also found to have high ratios of citric acid to malic acid and high ratios of hexose to sucrose. Some Galia type melons, such as MG 755, were also found to have high citric acid contents. Surprisingly, according to the present invention, in a cross between a Japanese-type melon and a Charentais-type melon (Prince PF in Table 2), the high citric acid content of the Japanese-type melon could be disassociated from the high hexose to sucrose ratio and combined with the high sucrose to hexose ratio of the Charentais-type melon. The invention further recognized that variations in citric acid contents also exist among non-sweet accessions such as Faqqous and IND-35 (low citric acid content in Faqqous when compared to IND-35, table 2).

Also, although it was generally assumed in the art that low pH and high sugar accumulation were not frequent or even compatible in the same melon fruit (Stepanski et al (1999)), the inventors of the present invention have been able to combine that characteristics of pH and organic acid described above with desired sugars contents in the fruits (see e.g. Table 3).

TABLE 2

Variation in citric acid contents in various melon types and varieties
(Fruit analysis data trial Sarrians August 1997)

| Name | No. fruits | Ri | pH | Citric acid (mg/100 g) | Sucrose (g/100 g) | Hexoses Glucose | Glucose (g/100 g) | Fructose (g/100 g) | Total Sugar (g/100 g) |
|---|---|---|---|---|---|---|---|---|---|
| Lunastar (Charentais) | 6 | 11.8 | 6.8 | 159 | 6.7 | 3.2 | 1.6 | 1.6 | 9.2 |
| Yuca-18-3-8 | 8 | 10.5 | 6.7 | 286 | 3.8 | 4.2 | 2.3 | 1.9 | 8.0 |
| MG 755 OA | 4 | | 6.8 | 294 | 11.4 | 3.7 | 2.1 | 1.7 | 15.1 |
| Prince PF (Japanese X Charentais) | 5 | | 6.1 | 438 | 10.0 | 3.3 | 1.2 | 2.1 | 13.3 |
| Sancho | 4 | | | 409 | 3.7 | 4.1 | 2.1 | 1.9 | 7.8 |
| Fagouss Egypt | 10 | 3.8 | 5.6 | 35 | 0.1 | 1.9 | 0.9 | 1.0 | 1.9 |

TABLE 2-continued

Variation in citric acid contents in various melon types and varieties
(Fruit analysis data trial Sarrians August 1997)

| Name | No. fruits | Ri | pH | Citric acid (mg/100 g) | Sucrose (g/100 g) | Hexoses Glucose | Glucose (g/100 g) | Fructose (g/100 g) | Total Sugar (g/100 g) |
|---|---|---|---|---|---|---|---|---|---|
| Fagouss Jim MC Greigt | 6 | 3.3 | 5.2 | 62 | 0.1 | 2.1 | 0.9 | 1.2 | 2.2 |
| Fagouss Jordany | 11 | 3.7 | 5.1 | 125 | 0.1 | 2.1 | 0.9 | 1.2 | 2.2 |
| IND35-1 | 8 | 4.5 | 4.9 | 340 | 0.6 | 3.4 | 1.8 | 1.7 | 4.0 |

Ri: Brix, refractometer index, measuring soluble solids

TABLE 3

Sugar accumulation vs. pH
Statistical analysis of sugar accumulation (brix) versus pH in
F2 populations of a cross between IND-35 and YUCA or OGEL
(Agadir'98). The analysis shows no negative correlation between
brix values and the pH.

| | | pH < 5.5 | | pH > 5.5 | | ANOVA |
|---|---|---|---|---|---|---|
| | | RI (Brix) | pH | RI (Brix) | pH | P = 0.05 |
| IND35/YUCA-15 | NR plts | 68 | 68 | 22 | 22 | P = 0.98 |
| F2 | Maximum | 13.00 | 5.40 | 13.60 | 7.00 | No Significant |
| | Average | 8.03 | 4.53 | 8.01 | 5.85 | Difference |
| | Std. Deviation | 2.34 | 0.30 | 2.72 | 0.37 | in brix |
| | Minimum | 2.40 | 3.80 | 2.40 | 5.50 | Populations |
| IND35/OGEL-17 | NR plts | 98 | 98 | 39 | 39 | P = 0.65 |
| F2 | Maximum | 13.00 | 5.45 | 12.20 | 7.50 | No Significant |
| | Average | 7.75 | 4.70 | 7.93 | 5.97 | Difference |
| | Std. Deviation | 2.16 | 0.33 | 1.89 | 0.35 | in brix |
| | Minimum | 2.80 | 3.90 | 4.20 | 5.50 | Populations |
| IND.35 | NR plts | 29 | 29 | | | |
| | Maximum | 7.60 | 5.40 | | | |
| | Average | 5.45 | 4.63 | | | |
| | Std. Deviation | 1.18 | 0.31 | | | |
| | Minimum | 3.00 | 4.10 | | | |

The present invention further discloses the incorporation of a low pH trait in sweet *C. melo* backgrounds. The presence of the low pH trait in sweet *C. melo* backgrounds allowed to lower the pH and increase concentrations of organic acids in the fruit flesh and to combine desirable pH and citric acid contents with appropriate sugar concentrations and contents, resulting in pleasant, new tastes.

In one embodiment, a low pH trait is determined by a low pH gene. In one embodiment, a low pH gene is obtained from a wild melon accession or cultivar. In one embodiment, a wild melon accession or cultivar used as donor for the low pH gene comprises traits that facilitate the construction of commercial melons with acceptable agronomic characteristics and producing fruits with desirable taste. In one embodiment, such donor has the ability to accumulate relevant levels of sugars, such as sucrose. In one embodiment, such wild melon accession or cultivar has at least one of the following characteristics: non climacteric behavior, relative bigger fruit size and mesocarp component, crispy flesh.

In one embodiment, the low pH trait is obtained from line IND-35, representative seeds of which was deposited with NCIMB, Aberdeen, AB243RY, Scotland on Dec. 17, 2003 under Accession Number NCIMB 41202. This is a *C. melo* accession from India, which could be classified within botanical Var. chito, but it may be better classified as var. acidulus (Naudin, Pitrat et al.) because of its bigger size.

Citric acid is the main organic acid in the fruits of line IND-35 (up to 911 mg citric acid per 100 g fwt), while malic acid contents are below 50 mg per 100 g fwt. Surprisingly, fruits of IND-35 also have the ability to accumulate relevant levels of sucrose (up to 1.7 g sucrose per 100 g fwt and 5.6 g total sugars 100 g fwt after long fruit cycles, i.e after late harvest 50 or 53 days after fruit set). Table 2 also reports analysis of fruits of IND-35 showing a pH of about 4.9, a citric acid content of about 340 mg/100 g fresh weight (fwt), and a sugar content of about 4.0 g/100 g fwt.

In one embodiment, the low pH trait co-segregates with a molecular marker. In one embodiment, a molecular marker is a DNA fragment amplified by PCR, e.g. a SSR marker or a RAPDS marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait. In one embodiment, the instant invention discloses markers, which distinguish between different sources of low pH trait, and for the presence or absence of a low pH trait in a plant. For example, such marker is CMAT 141, described in Danin-Poleg et al. (2001) Theor. Appl. Genet. 102: 61-72 and Danin-Poleg et al. (2002) Euphytica 125: 373-384. Other examples of molecular markers are NE0585 and NE1746 disclosed herein (see Example 13). These markers are closely linked to the locus of the pH gene. Markers CMAT141 and NE0585 are on one side of the low pH gene, while marker NE1746 is on the other side of the low pH gene.

In one embodiment, the inventors of the instant invention have determined that various sources of low pH trait amplify DNA fragments of different length when the primers for the markers are used (acid fragments, see Example 14, Table 16). For example, in plants of Faggous as fragment of about 176 bp is amplified using for CMAT141. In plants of accessions PI414723, PI414724, PI161375 and PI124112 a fragment of about 175 bp is amplified. In contrast, in plants of IND-35, described herein, unique fragments of about 168 bp and of about 173 bp are amplified. Using marker NE0585, unique fragments of about 230 bp and about 232 bp are amplified for IND-35. Using marker NE1746, a unique fragments of about 127 bp is amplified for IND-35. Another fragment of about 124 bp is amplified for IND-35, which is for example absent in Faggous.

In one embodiment, plants not comprising the low pH trait were also analyzed using the primers described herein. A number of DNA fragments associated with the absence of the low pH trait were determined (basic fragments). For example, using the primers of CMAT141, fragments of about 169 bp, about 172 bp and about 178 bp long were detected in plants not comprising a low pH trait. Using the primers of NE0585, fragments of about 218 bp, about 229 bp, about 234 bp and about 239 bp long were detected. Using the primers of NE1746, fragments of about 133 bp, about 142 bp and about 145 bp long were detected. The skilled person would know how to analyze further plants not comprising the low pH trait and determine additional DNA fragments associated with the absence of the low pH trait.

The indicated sizes (in bp) are not absolute but relative to the other size products detected with the same primer pair. The real (exact) size of the amplified fragments (e.g. determined by sequencing) could be slightly different (+/−1 bp) of those indicated herein.

Accordingly, in one embodiment, the present invention discloses a *C. melo* plant comprising a DNA sequence, which is a template for amplification of a DNA fragment described herein using the primers described herein. In one embodiment, a DNA fragment of about 168 bp to about 178 bp is amplified from the DNA of said plant when the primers capable of identifying the CMAT141 marker are used. In one embodiment, a DNA fragment of 168 bp, 173 bp, 169 bp, 172 bp or 178 bp is amplified when the primers capable of identifying the CMAT141 marker are used. In one embodiment, a DNA fragment of less than 176 bp is amplified when the primers capable of identifying the CMAT141 marker are used. In one embodiment, a DNA fragment of less than 175 bp is amplified when the primers capable of identifying the CMAT141 marker are used. In one embodiment, a DNA fragment of about 218 bp to about 253 bp is amplified when the primers capable of identifying the NE0585 marker are used. In one embodiment, a DNA fragment of 230 bp, 232 bp, 218 bp, 229 bp, 234 bp or 239 bp is amplified when the primers capable of identifying the NE0585 marker are used. In one embodiment, a DNA fragment of about 121 bp to about 145 bp is amplified when the primers capable of identifying the NE1746 marker are used. In one embodiment, a DNA fragment of 124 bp, 127 bp, 133 bp, 142 bp or 145 bp is amplified when the primers capable of identifying the NE1746 marker are used.

In one embodiment, the inventors of the instant invention have separated the link between a DNA fragment indicative of a low pH trait and a low pH gene. In this case, a DNA sequence, which is a template for amplification of a basic fragment, is linked to a low pH trait. Accordingly, in one embodiment, the instant invention discloses a plant comprising a low pH trait co-segregating with markers indicative for a basic allele, in particular when using the markers disclosed herein. In one embodiment, a marker on one side of the pH gene is basic. In one embodiment, markers on both sides of the pH gene are basic. In one embodiment, fruits of such a plant comprise a pH within the ranges disclosed herein. In one embodiment, fruits of such a plant comprise the contents and compositions of sugars as described herein. In one embodiment, fruits of such a plant comprise the contents and compositions of organic acids as described herein. In one embodiment, fruits of such a plant comprise the pH, contents and compositions of sugars and contents and compositions of organic acids as described herein.

Accordingly, in one embodiment, the present invention discloses a *C. melo* plant comprising a DNA sequence, which is a template for amplification of a basic DNA fragment, linked to a low pH gene. In one embodiment, the present invention discloses a *C. melo* plant comprising a chromosome fragment comprising a DNA sequence, which is a template for amplification of a basic DNA fragment and a low pH gene. In one embodiment, such chromosome fragment is heterozygous or homozygous in said plant. Line SOLAZ/2 described herein is a representative example of such a *C. melo* plant. In SOLAZ/2, fragments of about 172 bp, about 229 bp and about 124 bp are amplified using the primers of markers CMAT141, NE0585 and NE1746, respectively.

In one embodiment, the present invention discloses a *C. melo* plant comprising a DNA sequence, which is a template for amplification of a basic DNA fragment, on one side of a low pH gene, a low pH gene, and a DNA sequence, which is a template for amplification of a basic DNA fragment, on the other side of the low pH gene, wherein both DNA sequence are linked to the pH gene in said plant. In one embodiment, the present invention discloses a *C. melo* plant comprising a chromosome fragment comprising a DNA sequence, which is a template for amplification of a basic DNA fragment, on one side of a low pH gene, the low pH gene and a DNA sequence, which is a template for amplification of a basic DNA fragment, on the other side of the low pH gene. In one embodiment, such chromosome fragment is heterozygous or homozygous in said plant. Line SOLAZ/1 described herein is a representative example of such a *C. melo* plant. In SOLAZ/1, fragments of about 172 bp, about 239 bp and about 142 bp are amplified using the primers of markers CMAT141, NE0585 and NE1746, respectively. Line YUSOL/3 described herein is another representative example of such a *C. melo* plant. In YUSOL/3, fragments of about 172 bp, about 239 bp and about 145 bp are amplified using the primers of markers CMAT141, NE0585 and NE1746, respectively.

Accordingly, the present invention discloses the use of a melon plant comprising a low pH trait to obtain a melon plant of the present invention. In one embodiment, the melon plant comprising a low pH trait further has the ability of accumulating relevant levels of sugars, for example sucrose. In one embodiment, the melon plant comprising a low pH accumulates high levels of citric acid. In one embodiment, the melon plant comprising a low pH accumulates low levels of malic acid. In one embodiment, the melon plant comprising a low pH is a plant of line IND-35 or a descendent thereof.

In one embodiment, the low pH trait is obtained from a descendent of said line IND-35. The skilled person recognizes that a low pH trait can also be obtained from other sources. In one embodiment, the low pH trait in such other sources is allelic to the low pH trait in IND-35. In one embodiment, a test is conducted to determine whether a line to be tested for a low pH gene comprises an allelic gene to that of line IND-35. Line IND-35 is used as a tester line in a cross with a line to be tested and the segregation ratio of the low pH phenotype is determined in the resulting progeny.

In one embodiment, a plant of line IND-35 is crossed with breeding melon lines, preferably having high citric acid contents and high levels of sugar. After each cross plants producing fruits having low pH are selected. Selection is also carried out for increased citric acid contents and high sugar contents. Examples of the introduction of the low pH trait into elite lines are disclosed in Examples 7-11.

In one embodiment, a molecular marker as disclosed hereinabove is used to transfer the pH trait in a desired background, in particular in method of increasing the citric acid content of a fruit of a melon plants as described herein. In one embodiment, plants for which a fragment corresponding to a low pH trait is amplified are selected and further used.

In one embodiment, a reduction of about 1 to about 2.5 pH units, in one embodiment about 1.5 to about 2.0 pH units, is obtained after the introduction of the low pH trait in a sweet *C. melo* plant, when compared to fruits of a melon not comprising the low pH trait, for example when compared to an isogenic or near-isogenic line not comprising the low pH trait. In one embodiment, the citric acid content in the flesh of a melon plant is multiplied by a factor of about 1.5 to about 3 upon introduction of a low pH trait in said melon plant, when compared to fruits of a melon not comprising the low pH trait, for example when compared to an isogenic or near-isogenic line not comprising the low pH trait. Mature fruits of the various plants are compared. For example, Table 1A and 1B show comparisons between melon comprising a low pH trait and melons not comprising a low pH trait, for example between YUSAZ X YUSOL and MILENIUM-DENEV F1, SOLAZ X YUSOL and SOLAR F1, Mehari/L53-L53 AZ A-L53 AZ B.

Accordingly, melon fruits of the present invention have higher concentrations of organic acids than comparable currently available melons not comprising the low pH trait (titratable acidity). In melon fruits of the present invention, variations in pH are more correlated with the composition (pKa of dominant acids) than with total concentration of organic acids. An increase in pH is generally observed during the late ripening process, and is concurrent with sucrose accumulation. This increase in pH is buffered by the content in organic acids. Low contents in organic acids result in high increases in pH and reduction in sour taste perception. For example, in melons with low citric content as some currently available Charentais-type melons, for example of climacteric turning type, this increase in pH can be over 1.0 pH unit (from pH 6.0 to 7.0). By contrast, higher contents in organic acids lead to reduced pH increases during the ripening process, and thus prevent or reduce the decline in sour taste perception, as for example in less climacteric, less turning melons.

Accordingly, in one embodiment, the present invention discloses melons fruits with more stable sour tart taste based on stable low pH and high citric acid content. In one embodiment, the present invention discloses melons fruits with an improved stability of the taste after ripening or post-harvest. The present invention also discloses a method of delaying or reducing the increase in pH in the fruit of a melon plant comprising increasing the content of organic acids in said fruit and introducing a low pH trait in a melon plant. In one embodiment, such method comprises introducing the low pH trait in a plant with low or non climacteric behaviour. In one embodiment, such method comprises introducing the low pH trait in a plant capable of producing a low or non turning fruit.

In one embodiment, the present invention also discloses melons fruits, which mature from an initial early ripe mild sour taste to a fruity and full flavored taste based on a moderate increase of pH (up to 0.5 pH units) and moderately elevated citric acid contents.

According to the present invention, a low pH trait is introduced in melon plants producing fruits with various contents and composition of sugars. In one embodiment, plants from the Japanese-Oriental type, such as YUCA, are used as a source of sugars. It is generally observed that accumulation of sugars, particularly sucrose, is a question of fruit cycle time understood as days after pollination, from fruit setting to fruit ripening. In one embodiment, melon plants producing fruits having an early and relevant sugar accumulation are used in the instant invention. For example, plants of the Galia type, such as cultivar OGEL, are used as a source of sugars. In one embodiment, melon plants producing fruits having potential for a high and fast accumulation of sucrose independently from the initial levels of hexoses are used in the instant invention. For example, plants of the Charentais type, such as L53, are used as a source of such a potential for sucrose accumulation.

Examples of the transfer of a low pH trait to elite lines are disclosed in the Examples below. Table 8 below also discloses melon plants obtained during the transfer to elite lines. However, other types of melons or other melons cultivars or varieties of the types mentioned above are used in the context of the present invention to construct melon plants according to the instant invention.

In one embodiment, a *C. melo* plant comprising a low pH trait is crossed to a *C. melo* plant of the Oriental type or of the Galia-type. For example the *C. melo* plant comprising a low pH gene is line IND-35. For example, the *C. melo* plant of the Oriental type is YUCA, and the *C. melo* plant of the Galia-type is OGEL, as described in Example 7 below. The resulting progenies are for example further crossed to *C. melo* plants of the Oriental type or of the Galia-type to obtain desired pH and contents and compositions of organic acids and sugars. This process is assisted by measurement of pH, organic acids and sugars, as disclosed herein. Alternative *C. melo* plants of the Oriental type or of the Galia-type can also be screened for desired characteristics and used as starting materials to obtain *C. melo* plants as described herein.

In one embodiment, a *C. melo* plant comprising a low pH trait is crossed to a *C. melo* plant of the Charentais-type, such as L53 as described in Example 11. Alternative *C. melo* plants of the Charentais-type can also be screened for desired characteristics and used as starting materials to obtain *C. melo* plants as described herein.

Other types of *C. melo* plants are also crossed to a *C. melo* plant comprising a low pH trait to obtain *melo* plants as described herein.

In one embodiment, the present invention discloses a plant capable of producing a fruit, the characteristics of which remain stable after a fruit reaches maturity and is kept on the plant or when the fruit is harvested and kept in storage. In one embodiment, the characteristics of a fruit described herein remain stable during the commercial post-harvest life of the fruit. This allows storing or shipping a fruit of the present invention for extended periods of time without loosing its organoleptic characteristics and aromas.

In one embodiment, the pH of a fruit of the instant invention remains stable after a fruit reaches maturity. In one embodiment, the pH of a fruit of the instant invention remains within a range of about 4.2 to about 5.6 after a fruit reaches maturity. In one embodiment, the citric acid content of a fruit of the present invention remains stable after a fruit reaches maturity. In one embodiment, the citric acid content of a fruit of the present invention remains at or above 400 mg per 100 g fwt after a fruit reaches maturity. In one embodiment, the malic acid content of a fruit of the present invention remains stable after a fruit reaches maturity. In one embodiment, the ratio citric acid to malic acid of a fruit of the present invention remains stable after a fruit reaches maturity. In one embodiment, the ratio citric acid to malic acid remains greater than 4.4 after a fruit reaches maturity. In one embodiment, such characteristics remain with the ranges described herein after a fruit reaches maturity. In one embodiment, these characteristics remain on within about 70% to about 130% of the values of the characteristics measured when the fruit reaches maturity, in one embodiment within about 80% to about 120% of the values of the characteristics measured when the fruit reaches maturity, in one embodiment within about 90% to about 110% of the values of the characteristics measured when the fruit reaches maturity. In one embodiment, the present invention discloses a plant capable of producing a fruit, the characteristics of which remain stable after a fruit reaches maturity when kept on the plant, or when harvested and kept in storage In one embodiment, the present invention discloses a plant capable of producing a fruit, the characteristics of which remain stable for at least 2 days when the fruit is kept on the plant, in one embodiment for at least 3 days when the fruit is kept on the plant, in one embodiment for at least 4 days when the fruit is kept on the plant. In one embodiment, the present invention discloses a plant capable of producing a fruit, the characteristics of which remain stable for at least 5 days when kept in storage at 20° C., in one embodiment for at least 7 days when kept in storage at 20° C., in one embodiment for at least 9 days when kept in storage at 20° C. In one embodiment, the present invention discloses a plant capable of producing a fruit, the characteristics of which remain stable for at least 7 days when kept in storage at 8-12° C. followed by at least 2 days at 20° C., in one embodiment for at least 12 days when kept in storage at 8-12° C. followed by at least 2 days at 20° C., in one embodiment for at least 26 days when kept in storage at 8-12° C. followed by at least 2 days at 20° C. Typically, after its harvest a fruit may remain under field conditions for several hours until its is stored in the conditions set forth herein.

Examples of the evolution of the characteristics of a fruit of a plant of the present invention when kept on the plant are shown in Example 15, Table 17. Examples of the evolution of the characteristics of a fruit of a plant of the present invention after post harvest storage are shown in Example 16, Tables 18 and 19.

In one embodiment, melons can be described as short shelf life (SLS), medium shelf life (MSL) or long shelf life (LSL). Examples of LSL melons are Milenium, Piel de Sapo, Italo and non turning Charentais LSL. Examples of MSL melons are Galia and turning Charentais MSL. Examples of short shelf life (SSL) melons are classical Charentais.

Typically, the life of a fruit of a SSL melon on the plant is about 1 to about 2 days. This means that fruits have to be harvested about every 1 to 2 days to avoid losses. Typically, the life of a fruit of a MSL melon on the plant is about 3 to about 4 days. This means that fruits are harvested about every 3 to 4 days to avoid losses. Typically, the life of a fruit of a LSL melon on the plant is more than about 5 days Typically a SSL melon can be stored for about 4 to about 7 days at 8-12° C. followed by an additional 2 days at 20° C., or for about 3 to 4 days at 20° C. Typically a MSL melon can be stored for about 7 to about 12 days at 8-12° C. followed by an additional 2 days at 20° C., or for about 5 to 10 days at 20° C. Typically a LSL melon can be stored for more than about 12 days at 8-12° C. followed by an additional 2 days at 20° C., or for more than about 10 days at 20° C.

In one embodiment, a plant of the instant invention is capable of producing a long shelf-life fruit (LSL) or a medium shelf-life fruit (MSL).

The inventors of the present invention have determined that the low pH trait and high citric accelerates the climacteric rise in a melon fruit after a fruit reaches maturity, especially in turning and climacteric melons. This leads to degradation of the fruit for example shown by a rapid increase in pH and malic acid content and a decrease in citric acid content. This is also shown by the appearance of mealy texture and alcoholic degradation. In turning and climacteric melons, the shelf life of the fruit is reduced, while this phenomenon is less perceptible in non-turning or/and non-climacteric melons. Accordingly, in one embodiment, a plant of the present invention is of a non-turning or low turning melon genotype. In one embodiment, a plant of the present invention is capable of producing a non-climacteric or low-climacteric fruit.

Accordingly, in one embodiment, the present invention discloses a *C. melo* plant with low or non-climacteric behaviour comprising a low pH gene. In one embodiment, a fruit of such *C. melo* plant further comprises the characteristic of sugar contents and compositions described herein. In one embodiment, a fruit of such *C. melo* plant further comprises the characteristic of organic acid contents and compositions described herein. In one embodiment, a fruit of such *C. melo* plant comprises a ratio of citric acid to malic acid as described herein. In one embodiment, a fruit of such plant further comprises a pH as described herein.

In one embodiment, the present invention discloses a *C. melo* plant capable of producing a low-turning or non-turning fruit, wherein said plant comprises a low pH gene. In one embodiment, a fruit of such *C. melo* plant further comprises the characteristic of sugar contents and compositions described herein. In one embodiment, a fruit of such *C. melo* plant further comprises the characteristic of organic acid contents and compositions described herein. In one embodiment, a fruit of such *C. melo* plant comprises a ratio of citric acid to malic acid as described herein. In one embodiment, a fruit of such plant further comprises a pH as described herein.

In one embodiment, the inventors of the instant invention have identified that a low pH in the flesh of a melon fruit is associated with a very poor color intensity of the flesh of fruits with orange flesh. In particular, in the case of melon plants producing fruit with orange flesh, a slightly orange or pale orange color was observed (see e.g. Table 4). Surprisingly, the inventors of the present invention have been able to combine low pH and deep orange color in the fruit of a melon plant.

Table 4 shows that the color intensity of the fruits of line L53, a parent of Syngenta hybrid MEHARI, is deep to very deep orange (average of 5.17). Plants originating from a back-cross program to introduce the low pH trait in L53 but not comprising the low pH trait (L53*High pH) showed a slight decrease in both color intensity and pH (4.71 and 6.46). Plants originating from the back-cross program and comprising the low pH trait showed a further decrease in color intensity and pH. Plants with the low pH trait in homozygote stage (L53*Low pH) had the lowest rate for orange flesh color: 4.04. Plants with the low pH trait in heterozygote stage (L53*acid) have the intermediate rate for orange flesh color: 4.36. This indicates a linkage or phenotypic effect between low pH and pale orange flesh color. Plants were therefore selected for intense orange flesh color in presence of the low pH trait (rated in one embodiment at 4 or higher in the scale below, in one embodiment at 5 and higher, in one embodiment at 6).

In one embodiment, the present invention discloses a *C. melo* plant capable of producing fruit with pH of about 4.5 to about 5.6, wherein said fruit has orange flesh rated 4 or higher. In one embodiment, the orange color of said fruits is rated 5 and higher, in one embodiment 6. In one embodiment, the pH of said fruit is about 4.5 to about 5.4, in one embodiment about 4.8 to about 5.2. In one embodiment, said fruit comprises about 400 mg to about 900 mg citric acid per 100 g fwt. In one embodiment, the fruit comprises about 450 mg to about 750 mg citric acid per 100 g fwt. In one embodiment said fruit comprises a sugar content equal or above about 5 g per 100 g fwt, in one embodiment about 5.0 g to about 13.0 g sugar per 100 g fwt. In one embodiment, the fruit comprises about 6.0 g to about 12.0 g sugar per 100 g fwt. In one embodiment, the ratio citric acid to malic acid in said fruit is between about 4 and 30, in one embodiment between about 5 and about 15. In one embodiment, the ratio sucrose to hexoses in a fruit of said plant is about 1:1 and about 1:2.

A scale of: 1: white, 2: slightly orange, 3: pale orange, 4: orange, 5: deep orange, 6: very deep orange was used for the color rating (see table 4). In one embodiment, the color of the fruit is assessed using a spectrophotometer, such as a Minolta CM-2500d spectrophotometer.

TABLE 4

| Fruits Nr. | | Pale Orange 2 | 3 | 4 | 5 | Deep Orange 6 | |
|---|---|---|---|---|---|---|---|
| % of flesh colour intensity class per | | | | | | | |
| | | | | | | | Col avg |
| 5 | True L53 | | | | 83% | 17% | 5.17 |
| 14 | L53* High pH | | | 29% | 71% | | 4.71 |
| 91 | L53* acid | 0% | 7% | 55% | 34% | 4% | 4.36 |
| 244 | L53* low pH | 2% | 19% | 48% | 27% | 3% | 4.04 |
| pH average per flesh colour intensity class | | | | | | | |
| | | | | | | | pH avg |
| 5 | True L53 | | | | 6.90 | 6.64 | 6.85 |
| 14 | L53* High pH | | | 6.28 | 6.53 | | 6.46 |
| 91 | L53* acid | | 4.75 | 4.81 | 4.87 | 4.94 | 4.83 |
| 244 | L53* low pH | 4.53 | 4.64 | 4.76 | 4.73 | 4.65 | 4.72 |

"L53* acid": means acid phenotype excluded proved fix Low pH homozigotes

In one embodiment, characteristics of melon fruits of the present invention are measured on fruits harvested at maturity, i.e. mature or ripe fruits. The concrete composition of a melon fruit, and therefore its taste, is affected by the ripening stage, at which it is harvested. Sugars and organic acids accumulation in melon fruits are dynamic processes. As the fruit is approaching maturity their accumulation starts. As the ripening process advances, each of these compounds follows a time-specific pattern of accumulation or degradation, which is also affected by environmental and growth conditions. The person skilled in the art knows how to recognize a mature melon fruit and understand criteria defining the maturity of a melon fruit.

In one embodiment, one of the following external maturity markers is used for identification of ripening in sweet melon:
  Senescence of the side fruit leaf (the melon fruit sets in flower axillar to the peduncle insertion of one leaf named side leaf fruit). The side fruit leaf becomes necrotic.
  Fruit skin color changes (turning color green to yellow in Galia type, gray to creamy-yellow in Charentais type, or increase in yellow component in Piel de Sapo type).
  Peduncle dehiscence (specially for Shipper melon, less for Charentais, less for Galia).
  Decline in fruit shell firmness, particularly in the blossom end area.

In one embodiment, "maturity" includes the ripening physiological process between the stages identified as "2" for "Early—Partial mature" and "4" for "Late—Fully mature".

In one embodiment, the Early-Partial mature stage in melons is identified with the initial accumulation of sucrose contents at or over 2 g per 100 g fwt of sucrose. In one embodiment, this is associated with the peaking of citric acid and reducing sugars (glucose plus fructose) contents, and a typical ripe fruit flesh pigments and texture. In one embodiment, the Late—Fully mature stage in melons is defined with the end of peaking sucrose sugars contents. It is also defined as before the degradation process starts, such as loss of fruit flesh consistency, fast declines in glucose, citric acid contents or increases in malic acid contents. Accordingly, in one embodiment, maturity of a fruit starts when the sucrose content in the fruit reaches 2 g per 100 g fwt. In one embodiment, maturity lasts until no more increase in sucrose content is observed.

The measurements disclosed herein are usually averages of measurements or data taken from a number of fruits. It is understood that, in any sample, individual fruits of a plant or fruits from individual plants do not lie within the ranges described, because of variations generally observed while growing melon plants. In one embodiment, the characteristics of melon fruits described herein are measured using fruits grown in the conditions described herein or under similar conditions (e.g. in Example 6, Tables 5-7 below). In one embodiment, a figure for a characteristic according to the instant invention is an average taken from fruits from plastic house staked plants (one fruit per plant in staked plants).

In one embodiment, a plant of the instant invention is an inbred line, a dihaploid or a hybrid. In one embodiment, an inbred line comprises a low pH trait and the characteristics of organic acids, pH and sugars described herein. In this case, such inbred line is crossed with another melon plant, preferably another inbred line, to obtain a hybrid plant according to the instant invention. In one embodiment, the other inbred line in the cross is also capable of producing fruit having high citric acid contents and/or high sugar contents. Representative inbred lines according to the present invention are disclosed in Table 1A.

In one embodiment, a plant of the instant invention is a hybrid plant. In this case, some of the characteristics of low pH, high citric acid content and high sugar content are contributed from one of the parent, while the remaining ones are contributed by the other parent. In a one embodiment, one parent in the cross produces fruit having high citric acid content, high sugar content but having high pH (e.g. around pH 6.5), while the other parent in the cross produces fruit having low pH. In one embodiment, fruits of the other parent also have high citric acid content. Representative hybrids according to the present invention are disclosed in Table 1B. As used herein, the term "plant" includes plant cells, plant protoplasts, plant cell of tissue culture from which melon plants can be regenerated, plant calli, plant clumps, and plant cells that are intact in plants or parts of plants, such as pollen, flowers, leaves, stalks, and the like. In one embodiment, a plant of the instant invention is capable of producing edible melon fruits. The mesocarp represents the edible part of the melon fruit (flesh). The mesocarp surrounds the seed cavity, which is itself surrounded by the rind (or shell). The mesocarp of a fruit according to the present invention preferably has a thickness of more than 2 cm and preferably represents more than 50% of the total fruit fresh weight. In one embodiment, the flesh of a fruit of a melon plant of the present invention has a green, white, yellow or orange flesh.

In one embodiment, the present invention provides regenerable cells for use in tissue culture of a plant of the present invention. The tissue culture is capable of regenerating plants having the characteristics of a plant of the present invention.

Preferably, the regenerable cells in such tissue cultures are immature embryos, protoplasts, meristematic cells, callus, pollen, leaves, anthers, roots, root tips, or flowers. Still further, the present invention provides melon plants regenerated from the tissue cultures of the invention. Examples of regeneration protocols are disclosed in U.S. Pat. No. 6,420,631. The present invention further provides a method of asexually propagating a plant of the present invention comprising collecting a tissue of a plant of the present invention, cultivating said tissue to obtain proliferated shoots, rooting said proliferated shoots to obtain rooted plantlets. The present invention further discloses a method to produce seed of a plant according to the instant invention comprising obtaining a plant of the present invention, self-pollinating said plant or crossing said plant with another melon plant, and harvesting progeny seed. The present invention further discloses a method for producing a fruit comprising planting a plant according to the present invention, growing said plant and harvesting a fruit, wherein said fruit comprises the characteristics described herein. The method further comprises storing said fruit, for example as described herein. The method further comprises shipping said fruit. In one embodiment, the characteristics of said fruit described herein remain stable during the storage of said fruit. In one embodiment, the characteristics of said fruit described herein remain stable during the storage of said fruit.

Some characteristics of a number of *C. melo* types and lines are described below. These characteristics are examples for the various melon types and lines, and are not meant to be limiting but are illustrative of the various melon types and lines. Variations from these characteristics may occur.

Melon Type Charentais:

Fruit: Shape round to hight round; Size 600 to 1200 grs; Rind: White-Gray with Green-Gray sutures, smooth skin (smooth or slightly netted skin). Orange, melty, very aromatic sweet flesh, climacteric. Some Charentais varieties have reduced climateric phase and not turning rind colour.

Var LUNASTAR: Lunastar is monoecious hybrid from Nunhems in Charentais type.

Melon Type Japanese:

Fruit: Shape round to hight round; Size 700 to 1500 grs; Rind: White-Gray netted skin, (exceptionally sutured). Green-Yellow (exceptionally orange), from cryspy to melty and few aromatic and very sweet flesh, only in cases. Long cycle non climacteric.

Var YUCA: Andromonoecious hybrid in Japanese type green flesh.

Var PRINCE: Andromonoecious hybrid in Japanese type orange flesh.

Melon Type Galia:

Fruit: Shape round to hight round; Size 600 to 1500 grs; Rind: Green tuning yellow netted skin. Green-White, melty, aromatic sweet flesh. Short cycle Medium shelf life, climacteric. Var MG.755: Andromonoecious hybrid in Galia type. Very short fruit cycle with high brix.

Melon Type Piel De Sapo:

Fruit: Shape Ovoid to oblong-eliptic; Size 2 to 5 Kgrs; Rind: Golden Green spotted, few longitudinal netted skin. White, crispy, juicy and aromatic sweet flesh. Medium fruit cycle Long shelf life, Non climacteric.

Var Sancho: Andromonoecious hybrid in Piel de sapo type. Golden rind with high brix.

Melon type Fagous:

Fruit: Shape Medium short cylindrical; Size 300 to 1000 grs; Rind: Green skin. White, crispy, non sweet flesh. For consumption green in salad. Monoecious IND 35: Fruit: Shape Long pear—ovoid; Size 300 to 1000 grs; Rind: Light Green spotted skin yellow at maturity. White, crispy, non sweet flesh. For consumption green in salad. Monoecious. Syngenta Seeds line, non climacteric.

YUSOL: Shape round to hight round; Size 600 to 1300 grs; Rind: Yellow few netted with light green sutures skin. Green-white, melty, few aromatic sweet non acid flesh. Short cycle Medium shelf life, non turning low climacteric. Andromonoecious Syngenta Seeds Line.

YUSAZ A: Shape round to hight round; Size 600 to 1300 grs; Rind: White-gray few netted with Green-Gray sutures skin. Green, specially crispy, few aromatic, sweet and acid flesh. Short cycle Medium-long self life, non turning, low to medium climacteric. Andromonoecious Syngenta Seeds Line.

YUSAZ B: Shape round to hight round; Size 600 to 1300 grs; Rind: Yellow netted with Green-Gray sutures skin. Green, specially crispy, few aromatic, sweet and acid flesh. Long cycle, long self life, non turning low climacteric. Andromonoecious Syngenta Seeds Line.

MILENIUN-DENEV: Shape round to hight round; Size 600 to 1500 grs; Rind: Yellow netted non sutured skin. Green-White, crispy, non aromatic, non acid and sweet flesh. Long cycle, non turning, long self life, non climacteric. Andromonoecious Syngenta Seeds Hybrid.

SOLAZ/1: Shape round to hight round; Size 700 to 1400 grs; Rind: Yellow few netted with light green sutures skin. White, crispy, few aromatic sweet and acid flesh. Short cycle, long self life, non turning, very low climacteric. Andromonoecious Syngenta Seeds Line.

SOLAZ/2: Shape round to hight round; Size 600 to 1300 grs; Rind: Yellow few netted with light green sutures skin. White, crispy, few aromatic sweet and acid flesh. Short cycle long self life, non turning, very low climacteric. Andromonoecious Syngenta Seeds Line.

MEHARI: monoecious hybrid from Syngenta in Charentais type. Turning medium shelf life.

L53: andromonoecious line from Syngenta in Charentais type. Turning medium shelf life. Small size round flat shape. Derived from var LUNASTAR, a monoecious hybrid of Nunhems in turning Charentais type.

TD: monoecious line from Syngenta in Charentais type. Non turning and long shelf life. Derived from var TORNADO, a monoecious hybrid from Limagrain in non turning Charentais type.

All references cited herein are incorporated by reference in the application in their entireties. When ranges are disclosed herein, it is understood that all the individual numbers falling within these ranges are also part of the invention.

The following examples are intended to provide illustrations of the application of the present invention. The following examples are not intended to completely define or otherwise limit the scope of the invention.

EXAMPLES

Example 1

Preparation of Melon Extracts

A wedge of ca. 400 g was taken from a melon fruit, the seeds and the skin (1 cm thickness) were removed. The flesh was cut in small parts, which were blended for 30 seconds in a Warring blender until a smooth slurry was obtained. The slurry was filtrated over a Whatman paper filter, the juice centrifugated in an Eppendorf centrifuge at 10.000 g and stored at −20 degrees Celcius.

Example 2

Determination of Citric Acid Content

Samples as prepared in Example 1 were incubated with citrate lyase (CL) to convert citric acid to oxaloactate and acetate. In the presence of the enzymes malate dehydrogenase (MDH) and lactate dehydrogenase (LDH), oxaloacetate and its decarboxylated derivative pyruvate were reduced with NADH to respectively L-malate and L-lactate. The decrease of NADH is proportional with the quantity of citric acid in the sample and can be determined at 340 nm. The assay was conducted in microplates. 20 µl of diluted sample was added to a microtiterplate. 200 µl of assay mixture containing NADH, MDH and LDH was added and mixed to the plate. The reaction was started with 15 µl of start-solution containing CL. The plate was mixed and let the reaction proceed for 1 hour. Absorbance values were measured at 340 nm with a microtiterplate reader (Biotek EL808 reader with KCJunior software and computer). A calibration curve was used to calculate the concentration citric acid in the samples. The enzymes were purchased from Roche Diagnostics.

Example 3

Determination of Malic Acid Content

Samples as prepared in Example 1 were incubated with L-malate dehydrogenase (MDH) and $NAD^+$ to convert L-malate to oxaloacetate. The equilibrium of the reaction is on the side of malate but was forced to the side of oxaloacetate with hydrazine by means of derivatization. NADH formed during the assay is proportional with the malic acid content in the samples. NADH can be determined at 340 nm as a measure for malic acid.

The assay was conducted in microplates. 20 µl of diluted sample was added to a microtiterplate. The reaction was started by adding 200 µl of assay mixture containing hydrazine, MDH and $NAD^+$ at pH 10. The plate was mixed and the reaction was allowed to proceed for 1 hour. Absorbance values were measured at 340 nm with a microtiterplate reader (Biotek EL808 reader with KCJunior software and computer). A calibration curve was used to calculate the concentration malic acid in the samples. MDH was purchased from Roche Diagnostics.

Example 4

Determination of Glucose, Fructose and Sucrose Contents

Glucose:

Glucose was determined with the enzymes hexokinase and glucose-6-phosphate dehydrogenase (G-6-PDH). Glucose was phosphorylated with hexokinase to glucose-6-phosphate (G-6-P) and subsequently dehydrated to 6-phosphogluconate with the aid of NADP and G-6-PDH (reactions 1 and 2, respectively). The concentration of formed NADPH (the H-acceptor) is quantitatively related to the initial glucose concentration and was measured at 340 nm in the UV range of the light spectrum.

Fructose:

Fructose was determined in the same assay. Fructose was phosphorylated to fructose-6-phosphate (F-6-P) with the enzyme hexokinase. F-6-P was converted to G-6-P with the enzyme phosphoglucose-isomerase (PGI) and subsequently in 6-PG as described in reaction 2 above.

Sucrose:

Sucrose was converted to glucose and fructose with the enzyme β-fructosidase. Formed glucose was determined according to the reactions 1 and 2 as described above. The determinations were conducted in microtiterplates, absorbance values are measured with a microtiterplate reader (Biotek ELx808 with data collection software and computer). Enzymes were purchased from Roche Diagnostics.

Example 5

Measurements of pH

The pH of samples as described in Example 1 was determined using a CRIMSON GLP21 pH meter calibrated to pH4 and pH7 with standard solutions.

Example 6

Growth Conditions of Melons Plants

Melon plants were grown under different conditions at different locations (see table 5 below). The dates of the trials are shown in Table 6 and the growing conditions in the different trial are described in Table 7.

TABLE 5

| | Description of trials | | | | | | |
|---|---|---|---|---|---|---|---|
| LOCATION IN SPAIN | | CROP TYPE | | CONDITIONS | | | |
| TORREPACHECO T. St | EL EJIDO T. St. | VINE BEES POLLINATION | STACKED HAND POLLINATION | OPEN FIELD | PLASTIC- HOUSE | SOIL | SUBSTRATE HYDROPONIC |
| FA02PS | X | | X | | X | | X |
| SP03PV | X | X | | | X | X | |
| SP03PS | X | | X | | X | | X |
| SP03OF | X | | X | | X | | X | |
| SU03PS | | X | | X | | X | | X |
| FA03PS | | X | | X | | X | | X |

FA: Fall,
SP: Spring,
SU: Summer,
PS: Plastic house staked crop,
PV: Plastic house vine crop

TABLE 6

Trial dates
TRIAL DATES

| | SOWING | TRANSPLANTING | 1ST POLLINATION | MEDIUM HARVEST |
|---|---|---|---|---|
| FA02PS | Aug. 1, 2002 | Aug. 19, 2002 | Sep. 1, 2002 | Oct. 30, 2003 |
| SP03PV | Jan. 18, 2003 | Feb. 18, 2003 | Apr. 4, 2003 | May 15, 2003 |
| SP03PS | Feb. 18, 2003 | Mar. 18, 2003 | Apr. 18, 2003 | May 30, 2003 |
| SP03OF | Mar. 10, 2003 | Apr. 11, 2003 | May 20, 2003 | Jun. 28, 2003 |
| SU03PS | Jul. 24, 2003 | Aug. 8, 2003 | Aug. 20, 2003 | Oct. 6, 2003 |
| FA03PS | Aug. 7, 2003 | Aug. 22, 2003 | Sep. 8, 2003 | Nov. 3, 2003 |

Herein, SP03OF1 refers to analytical data of fruits harvested on Jun. 20, 2003. SP03OF2 refers to fruits harvested Jul. 4, 2003.

TABLE 7A

Growing conditions for FA02PS
Location: EL EJIDO T. St.
PLASTIC-HOUSE

| | Week no. 2002 | | | | |
|---|---|---|---|---|---|
| | 29/30/31/32 | 33/34/35/36 | 37/38/39/40 | 41/42/43/44 | 45/46/47/48 |
| temperature-day | 31.5 | 31 | 28.6 | 22.4 | 18.4 |
| temperature-night | 25 | 23.1 | 22.4 | 17.8 | 14.4 |
| temperature-24 hours | 28.8 | 27.4 | 25.5 | 19.8 | 18 |
| R. Humidity-day % | 51 | 47 | 55 | 78 | 84 |
| R. Humidity-night % | 73 | 72 | 78 | 89 | 90 |
| R. Humidity-24 h. % | 60 | 69 | 66 | 84 | 88 |

Weeks are numbered starting on January 1, week 29 being the 29$^{th}$ week of the year.

TABLE 7B

Growing conditions for SP03PV, SP03PS, SU03PS, FA03PS
Location: EL EJIDO T. St., PLASTIC-HOUSE

| | Week no. 2003 | | | | | | | |
|---|---|---|---|---|---|---|---|---|
| | 1/2/3/4 | 5/6/7/8 | 9/10/11/12 | 13/14/15/16 | 17/18/19/20 | 21/22/23/24 | 25/26/27/28 | 29/30/31/32 |
| temperature-day | 15.9 | 16.7 | 25.1 | 26.9 | 26.9 | 31.2 | 37.4 | 37.1 |
| temperature-night | 10.4 | 11.1 | 17.9 | 20.3 | 21.9 | 25.6 | 28.6 | 28.5 |
| temperature-24 hours | 12.6 | 13.5 | 21.4 | 23.8 | 24.8 | 28.9 | 33.9 | 33.5 |
| R. Humidity-day % | 71 | 59 | 46 | 53 | 63 | 54 | 38 | 32 |
| R. Humidity-night % | 91 | 83 | 64 | 68 | 73 | 67 | 57 | 46 |
| R. Humidity-24 h. % | 83 | 73 | 55 | 61 | 67 | 59 | 45 | 38 |

| | Week no. 2003 | | | |
|---|---|---|---|---|
| | 33/34/35/36 | 37/38/39/40 | 41/42/43/44 | 45/46/47/48 |
| temperature-day | 30.9 | 25.3 | 20.8 | 19 |
| temperature-night | 25.1 | 21.8 | 17.9 | 15 |
| temperature-24 hours | 28.3 | 23.6 | 19.2 | 16.7 |
| R. Humidity-day % | 60 | 82 | 89 | 86 |
| R. Humidity-night % | 80 | 89 | 96 | 99 |
| R. Humidity-24 h. % | 69 | 86 | 92 | 93 |

TABLE 7C

Growing conditions for SP03OF
TORREPACHECO T. St.
OPEN FIELD

| | Week no. 2003 | | | | |
|---|---|---|---|---|---|
| | 9/10/11/12 | 13/14/15/16 | 17/18/19/20 | 21/22/23/24 | 25/26/27/28 |
| Temperature Max | 28.0 | 36.0 | 34.0 | 33.0 | 37.0 |
| Temperature avg. Max | 19.9 | 26.2 | 27.0 | 28.0 | 34.5 |

TABLE 7C-continued

Growing conditions for SP03OF
TORREPACHECO T. St.
OPEN FIELD

| | Week no. 2003 | | | | |
|---|---|---|---|---|---|
| | 9/10/11/12 | 13/14/15/16 | 17/18/19/20 | 21/22/23/24 | 25/26/27/28 |
| Temperature Med | 14.3 | 20.1 | 19.9 | 22.1 | 27.1 |
| Temperature avg. Min. | 8.8 | 14.0 | 12.7 | 16.2 | 19.7 |
| Temperature Min. | 5.0 | 8.0 | 9.0 | 12.0 | 17.0 |

Example 7

Transfer of the Low pH Trait to Elite Lines

1. Line IND-35 was crossed with a selected set of Syngenta elite lines in the El Ejido Trial Station (Spain).

The selected lines were:

a).—YUCA-15: Selected because of high potential for sugars accumulation in medium long cycle (time from fruit set to fruit ripening). YUCA is a proprietary Syngenta Seeds line obtained through 5 generations of self-pollination. It is a Japanese Rocky melon type, non turning and very low climacteric.

b).—OGEL-17: Selected because of medium short cycle (time from fruit set to fruit ripening) and medium high potential for sugars accumulation. This line is a proprietary Syngenta Seeds line obtained through 10 generations of self-pollination from a breeding F1 from cross between parental lines of commercial hybrids GUSTAL and RADICAL (Syngenta Seeds). It is a GALIA melon type, turning and medium climacteric.

F1 crosses produced self-pollinated F2 descendent generation. The F2 fruits were selected for low pH and sugar (Table 8A).

2. Both F2 populations were grown and cross pollinated plant by plant with a new selected set of Syngenta elite lines:

a).—IND35/YUCA-15 F2 population was crossed with MG.755-68 (755), a proprietary Syngenta Seeds line obtained through 5 generations of self-pollination from a commercial hybrid BETULO (Syngenta Seeds). It is a GALIA turning and medium climacteric melon type selected for the purpose because of green flesh, high sugars, short cycle and relatively high citric acid content.

b).—IND35/OGEL-17 F2 population was crossed with SEN19C8 (SN8). This line is a proprietary Syngenta Seeds line, non turning and very low climacteric, obtained through 6 generations of self-pollination of a commercial hybrid EARLS SEINU (Yae Nogey Seeds Co. Isahaya, Nagasaki, Japan). It is a Japanese Rocky melon type selected for the purpose because of high sugars and netting.

In these populations, the single dominance genetic regulation for the Low pH trait was verified and that no linkage existed between sugar accumulation and said Low pH. (Table 3). From each populations (150 plants each), recombinants including the higher R.I. Brix degree and the lowest pH were selected. Cross-pollinated seed progeny was collected.

The cross progenies selected from F2 population a) included the plants identified as:
755YUCIND-19, 755YUCIND-49, 755YUCIND-75.

The one selected from F2 population b) included the plant identified as:
SN80GLIND-03.

755YUCIND lines were selected for sucrose accumulation. SN80GLIND was selected for citric acid accumulation. These cross progenies were grown and produced data for pH, sugars and organic acid contents. Lines combining high sugars, low pH and high citric acid content were selected. The analysis of the selected plants is shown in Table 8B.

Table 8: Analysis of intermediates

TABLE 8A

Analytical Data extract for selected plants in F2 (Agadir Autumn 1998)

| FEMALE | pH | BRIX | Genotype |
|---|---|---|---|
| YUCA-15.071.xIND35-1)-49. | 4.30 | 13.0 | Aa |
| YUCA-15.071.xIND35-1)-75. | 4.10 | 12.4 | Aa |
| YUCA-15.071.xIND35-1)-19. | 4.05 | 10.4 | AA |
| OGEL-17.974.xIND35-1)-03. | 4.57 | 11.8 | Aa |

TABLE 8B

Analytical Data extract for progeny B1F1 (El Ejido Spring 1999)

| MALE | FEMALE | pH | Citric acid (mg/100 g) | Malic acid (mg/100 g) | Glucose (g/100 g) | Fructose (g/100 g) | Sucrose (g/100 g) | Total sugar (g/100 g) | Brix R.I. | Nr. Fruits |
|---|---|---|---|---|---|---|---|---|---|---|
|  |  | 4.7 | 773 | 52 | 2.3 | 2.4 | 1.7 | 6.3 | 10.0 |  |
|  |  | 4.5 | 930 | 48 | 1.8 | 2.0 | 4.4 | 8.2 | 12.0 |  |
| SN8 | OGLIND-03. | 4.7 | 809 | 56 | 2.0 | 2.2 | 2.4 | 6.6 | 10.2 | 5 |
|  |  | 5.0 | 540 | 45 | 2.6 | 2.7 | 1.7 | 6.9 | 10.0 |  |
|  |  | 5.0 | 619 | 39 | 1.7 | 2.4 | 3.3 | 7.4 | 11.5 |  |
| 755 | YUCIND-49. | 4.8 | 535 | 67 | 2.0 | 2.5 | 1.8 | 6.3 | 9.9 | 5 |
|  |  | 5.0 | 549 | 38 | 2.5 | 2.7 | 2.7 | 7.9 | 12.0 |  |
|  |  | 5.4 | 564 | 52 | 2.6 | 2.7 | 2.2 | 7.4 | 11.0 |  |
| 755 | YUCIND-75. | 5.3 | 568 | 40 | 2.3 | 2.5 | 2.6 | 7.5 | 10.7 | 3 |
|  |  | 5.5 | 624 | 44 | 1.5 | 2.2 | 4.5 | 8.2 | 12.0 |  |
|  |  | 4.7 | 648 | 53 | 1.9 | 2.0 | 3.7 | 7.6 | 13.0 |  |
| 755 | YUCIND-19. | 5.1 | 569 | 44 | 1.7 | 2.1 | 3.3 | 7.2 | 11.1 | 8 |

TABLE 8C

Analytical Data extract for progeny B2&3F1 (El Ejido Autumn 1999)

| MALE | | FEMALE | pH | Citric acid (mg/100 g) | Glucose (g/100 g) | Fructose (g/100 g) | Sucrose (g/100 g) | Total Sugar (g/100 g) | Brix R.I. | Nr. Fruits |
|---|---|---|---|---|---|---|---|---|---|---|
|  |  |  | 4.7 | 802 | 2.5 | 2.5 | 2.9 | 7.9 | 12.5 |  |
|  |  |  | 4.7 | 1036 | 2.3 | 2.4 | 3.7 | 8.4 | 14.5 |  |
|  |  |  | 5.1 | 594 | 2.5 | 2.6 | 2.4 | 7.4 | 12.0 |  |
| IOTYU | SN8 | OGLIND-03. | 4.7 | 771 | 2.3 | 2.4 | 2.4 | 7.1 | 12.6 | 9 |
| 755 | 755 | YUCIND-19. | | | | | | | | |
| YUCA64 | 755)2 | YUCIND-19. | | | | | | | | |

TABLE 8D

Analytical Data extract for progeny B3F1&2 (Torrepacheco Spring 2000)

| MALE | FEMALE | | | pH | Citric acid (mg/100 g) | Glucose (g/100 g) | Fructose (g/100 g) | Sucrose (g/100 g) | Total Sugar (g/100 g) | Brix R.I. | Nr. Fruits |
|---|---|---|---|---|---|---|---|---|---|---|---|
| SOLAR-19 | IOTYU | SN8 | OGLIND-03. | | | | | | | | |
| SOLAR-19 | IOTYU | SN8 | OGLIND-03. | 4.14 | 725 | 1.9 | 1.6 | | | 15.0 | 13 |
| IOTYU | IOTYU | SN8 | OGLIND-03. | 4.73 | 523 | 1.8 | 1.2 | | | 14.3 | 3 |
| | YUCA64 | 755)2 | YUCIND-19. | 4.87 | 566 | 2.3 | 1.7 | | | 14.7 | 3 |

TABLE 8E

Analytical Data extract (El Ejido Autumn 2000)

| MALE | FEMALE | | | pH | Citric acid (mg/100 g) | Glucose (g/100 g) | Fructose (g/100 g) | Sucrose (g/100 g) | Total Sugar (g/100 g) | Brix R.I. | Nr. Fruits |
|---|---|---|---|---|---|---|---|---|---|---|---|
| | SOLAZ4.4.4 | | | 4.32 | 573 | 3.0 | 1.2 | | | 7.0 | |
| | SOLAZ4.7.2. | | | 4.44 | 564 | 3.3 | 1.1 | | | 11.0 | |
| | SOLAZ2.4.2 | | | 4.52 | 494 | 2.9 | 1.4 | | | 11.0 | |
| | SOLAZ2.4.5 | | | 4.43 | 474 | 2.7 | 1.0 | | | 10.0 | |
| YUCA-40 | IOTYU)2 | SN8 | OGLIND-03. | 4.48 | 453 | 2.5 | 1.0 | | | 12.0 | |
| | YUCA64 | 755)2 | YUCIND-19. | 4.79 | 904 | 4.8 | 1.8 | | | 13.0 | |

TABLE 8F

Analytical Data extract (El Ejido 2001)

| MALE | FEMALE | | | pH | Citric acid (mg/100 g) | Glucose (g/100 g) | Fructose (g/100 g) | Sucrose (g/100 g) | Total Sugar (g/100 g) | Brix R.I. | Nr. Fruits |
|---|---|---|---|---|---|---|---|---|---|---|---|
| | SOLAZ 1 | | | 4.59 | 940 | 2.3 | 2.9 | 4.1 | 9.4 | 11.0 | |
| | SOLAZ 2 | | | 4.63 | 770 | 2.5 | 2.7 | 1.3 | 6.6 | 8.0 | |
| YUSOL27 | YUCA-40 | IOTYU)2 | SNC8OGLIND-03. | 4.6 | 741 | 3.4 | 2.5 | 4.6 | 10.4 | 14.0 | |
| YUSOL27 | YUCA-64 | 755)2 | YUCIND-19. | 5.05 | 467 | 2.5 | 2.6 | 5.0 | 10.1 | 12.0 | |
| L53 | | 755 | YUCIND-75. | 4.80 | 718 | 1.3 | 2.2 | 1.6 | 5.1 | 7.0 | |
| L53 | | 755 | YUCIND-49. | 4.68 | 673 | 2.5 | 2.7 | 2.3 | 7.6 | 9.0 | |

Example 8

Trait Introgresion into SOLAZ

The Low pH trait was introgressed in white flesh non climacteric LSL melons with round shape and yellow sutured skin.

1. Selected SN80GLIND-103 progeny plants were crossed with IOTYU, a proprietary Syngenta Seeds line obtained through generations of self-pollination from the traditional open pollinated Japanese variety Makuwauri EIJYU (Nanto seed Co. Ltd, Kashiwara, Nara, Japan). It was selected because of non-climacteric, non turning, very high sugar content, high citric acid content, yellow rind.

2. Selected plants of the progeny from previous cross were crossed with SOLAR-19 a proprietary Syngenta Seeds line obtained through 5 generations of self-pollination from a commercial hybrid SOLARKING F1 (Nunhems Zaden B V, Haelen, Holland). It is a long shelf life, non turning Galia melon type selected for the purpose because of non climacteric, very high sugar content, white flesh, yellow and netted rind.

Seven cycles of self-pollination were carried out from these cross progenies. The selection and fixation on the self-pollination progenies was done with analytical data for pH, sugars and organic acid contents (Table 8C and 8D). Fixed lines progenies were selected:

A) SOLAZ 1 selected as Low pH in combination for high sugar accumulation, powdery mildew tolerance, and plant with Summer growing adaptation (Table 8E and F).

B) SOLAZ 2 selected as Low pH with combination for medium sugar accumulation, and plant with Spring growing adaptation (Table 8E and F).

3. Progenies SOLAZ 1 and SOLAZ 2 were used as males pollinators for crosses with three proprietary Syngenta Seeds lines, YUSOL 1, 2 & 3, obtained through 6 generations of self-pollination from a breeding hybrid MD.997 F1 from cross YUCA-15×SOLAR-48 both proprietary Syngenta Lines with origin indicated before.

The following F1 combinations were obtained:

A) YUSOL 1/SOLAZ 1; when using SOLAZ 1 as pollinator of lines YUSOL 1.

B) YUSOL 2/SOLAZ 1; when using SOLAZ 1 as pollinator of lines YUSOL 2.

C) YUSOL 3/SOLAZ 2; when using SOLAZ 2 as pollinator of lines YUSOL 3.

The analysis of these selected plants and commercially available controls is shown in Tables 9 and 10. The plants were grown under the conditions described in Example 6. The number of fruits tested in each experiment is shown (nr. Frt). The measurements were carried out as described in Example 1-5. The figures for sucrose (suc), hexoses (hex), and total sugars are in g per 100 g fresh weight (fwt). The figures for citric acid and malic acid are in mg per 100 g fresh weight (fwt).

TABLE 9A

SOLAZ

| | Growing conditions | nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| SOLAZ/2 | SP03PS | 6 | 2.41 | 1.70 | 3.41 | 0.34 | 5.82 | | 1.42 | 4.6 | 0.2 | 605 | 98 | 42 | 14 | 21 |
| | FA03PS | 37 | 1.43 | 0.81 | 5.12 | 0.36 | 6.55 | 1.34 | 3.58 | 4.7 | 0.2 | 576 | 86 | 52 | 11 | 15 |
| Average | | 43 | 1.92 | | 4.27 | | 6.19 | | 2.50 | 4.6 | | 590 | | 47 | 13 | |
| SOLAZ/1 | SP03PS | 4 | 2.90 | 0.86 | 3.93 | 0.42 | 6.83 | | 1.35 | 4.6 | 0.0 | 549 | 81 | 16 | 33 | 15 |
| | FA03PS | 35 | 1.85 | 1.18 | 5.88 | 0.33 | 7.73 | 1.60 | 3.17 | 4.5 | 0.1 | 663 | 107 | 35 | 19 | 17.5 |
| SOLAZ/1 | SP03PS | 4 | 2.01 | 0.22 | 3.82 | 0.20 | 5.83 | | 1.90 | 4.6 | 0.1 | 513 | 53 | 20 | 26 | 11 |
| | FA03PS | 16 | 1.80 | 0.74 | 5.32 | 0.27 | 7.13 | 1.25 | 2.95 | 4.5 | 0.1 | 591 | 83 | 52 | 11 | 10 |
| SOLAZ/1 | SP03PS | 5 | 2.35 | 0.88 | 3.79 | 0.37 | 6.14 | | 1.61 | 4.8 | 0.2 | 497 | 58 | 14 | 36 | 24 |
| | FA03PS | 7 | 2.02 | 1.36 | 6.14 | 0.35 | 8.15 | 1.65 | 3.04 | 4.5 | 0.1 | 664 | 86 | 28 | 24 | 24 |
| Average | | 71 | 2.16 | | 4.81 | | 6.97 | | 2.34 | 4.6 | | 579 | | 27 | 25 | |
| average SOLAZ/1 and /2 | | 114 | 2.10 | | 4.68 | | 6.77 | | | 4.6 | | 582 | | 27 | 22 | |

TABLE 9B

YUSOL

| | Growing conditions | nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| YUSOL/1 | SP03PS | 8 | 4.25 | 1.18 | 4.77 | 0.82 | 9.02 | | 1.12 | 6.0 | 0.3 | 295 | 85 | 47 | 6 | 10 |
| | FA03PS | 8 | 5.01 | 0.58 | 5.33 | 0.85 | 10.34 | 1.16 | 1.07 | 6.3 | 0.1 | 214 | 49 | 13 | 16 | 10 |
| Average/1 | | 16 | 4.63 | | 5.05 | | 9.68 | | 1.09 | 6.1 | | 255 | | 30 | 11 | |
| YUSOL/2 | SP03PS | 6 | 2.58 | 0.62 | 4.99 | 0.81 | 7.57 | | 1.94 | 5.8 | 0.1 | 297 | 83 | 424 | 1 | 3 |
| | FA03PS | 1 | 3.92 | | 7.30 | | 11.21 | | 0.54 | 5.9 | | 344 | | X | 0 | |
| Average/2 | | 7 | 3.25 | | 6.14 | | 9.39 | | 1.24 | 5.9 | | 320 | | | 1 | |
| YUSOL/3 | SP03PS | 6 | 5.04 | 1.43 | 4.04 | 0.81 | 9.08 | | 0.80 | 6.1 | 0.2 | 225 | 97 | 12 | 18 | 21 |
| | FA03PS | 5 | 6.23 | 0.67 | 5.64 | 0.47 | 11.87 | 0.54 | 0.91 | 6.2 | 0.2 | 218 | 62 | 9 | 24 | 10 |
| Average/3 | | 11 | 5.63 | | 4.84 | | 10.47 | | 0.85 | 6.2 | | 221 | | 11 | 21 | |
| Average 1, 2, 3 | | 34 | 4.50 | | 5.34 | | 9.85 | | 1.06 | 6.05 | | 265 | | 24 | 11 | |

TABLE 10A

Hybrid SOLAZ X YUSOL

| | Growing conditions | nr frt | suc avg | suc stdev | hex avg | hex stdev | tot. sugar avg | hex/suc inv activity | pH avg | pH stdev | citric avg | citric stdev | citric/ malic | malic avg | malic stdev |
|---|---|---|---|---|---|---|---|---|---|---|---|---|---|---|---|
| SOLAZ/1 X YUSOL/1 | SP03PV | 4 | 5.58 | 1.07 | 3.38 | 0.51 | 8.95 | 0.61 | 4.8 | 0.1 | 845 | 87 | 11240 | 0 | 2 |
| | SP03OF1 | 5 | 6.25 | 0.43 | 3.71 | 0.70 | 9.96 | 0.59 | 4.7 | 0.1 | 794 | 25 | 76 | 10 | 12 |
| | SP03OF2 | 5 | 6.90 | 0.60 | 2.55 | 0.19 | 9.44 | 0.37 | 4.8 | 0.1 | 679 | 50 | 47 | 14 | 8 |
| average/1 | | 14 | 6.24 | | 3.21 | | 9.45 | 0.52 | 4.8 | | 773 | | 97 | 8 | |
| SOLAZ/1 X YUSOL/2 | SP03PS | 3 | 3.45 | 0.24 | 4.68 | 0.52 | 8.14 | 1.36 | 4.7 | 0.1 | 697 | 32 | 45 | 16 | 12 |
| | SP03OF1 | 5 | 9.20 | 0.34 | 2.85 | 0.19 | 12.05 | 0.31 | 4.7 | 0.1 | 800 | 27 | 42 | 19 | 7 |
| | SP03OF2 | 4 | 7.01 | 1.30 | 2.69 | 0.40 | 9.70 | 0.38 | 4.8 | 0.1 | 744 | 46 | 39 | 19 | 4 |
| average/2 | | 12 | 6.56 | | 3.41 | | 9.97 | 0.68 | 4.7 | | 747 | | 42 | 18 | |
| SOLAZ/2 X YUSOL/3 | SP03PV | 4 | 4.41 | 0.72 | 3.20 | 0.44 | 7.61 | 0.73 | 4.7 | 0.2 | 863 | 62 | 100 | 9 | 18 |
| | SP03OF1 | 4 | 4.94 | 2.05 | 3.23 | 0.29 | 8.17 | 0.65 | 4.5 | 0.1 | 789 | 85 | 277 | 3 | 4 |
| | SP03OF2 | 5 | 9.42 | 1.09 | 2.04 | 0.37 | 11.46 | 0.22 | 4.9 | 0.1 | 694 | 63 | 109 | 6 | 2 |
| average/3 | | 13 | 6.26 | | 2.82 | | 9.08 | 0.53 | 4.7 | | 782 | | 162 | 6 | |
| Average | | 39 | 6.35 | | 3.15 | | 9.50 | 0.58 | 4.7 | | 767 | | 70 | 11 | |

TABLE 10B

Controls

| | Growing conditions | nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| SOLAR F1 | SP03PV | 6 | 5.28 | 0.93 | 2.52 | 0.32 | 7.80 | 0.92 | 0.48 | 6.1 | 0.08 | 500 | 51 | 28 | 18 | 26 |
| | FA03PS | 2 | 3.50 | 0.05 | 6.55 | 0.17 | 10.06 | 0.22 | 1.87 | 6.9 | 0.04 | 109 | 17 | X | 0 | 0 |
| Average | | 8 | 4.39 | | 4.54 | | 8.93 | | 1.17 | 6.48 | | 305 | | 35 | 9 | |

TABLE 10B-continued

Controls

|  | Growing conditions | nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| MILENIUM | SP03PV | 4 | 2.99 | 1.23 | 4.94 | 0.67 | 7.93 | 1.57 | 1.65 | 5.8 | 0.1 | 546 | 25 | X | 0 | 0 |
|  | SP03OF1 | 5 | 2.29 | 0.15 | 4.16 | 0.10 | 6.44 | 0.15 | 1.82 | 5.8 | 0.05 | 441 | 23 | X | 0 | 0 |
|  | SP03OF2 | 3 | 5.15 | 3.82 | 3.30 | 0.99 | 8.45 | 4.81 | 0.64 | 6.1 | 0.4 | 345 | 40 | X | 0 | 0 |
| Average |  | 12 | 3.47 |  | 4.13 |  | 7.61 |  | 1.37 | 5.88 |  | 444 |  | X | 0 |  |

Example 9

Trait Introgresion into YUSAZ A

The Low pH trait was introgressed in green flesh non climacteric LSL melons with round shape and yellow sutured skin.

1. Direct back-cross was made from line 755YUCIND-19 using as recurrent parent, line MG.755-68 indicated above.

Selected plants of the progeny from previous cross were crossed with YUCA-64 a proprietary Syngenta Seeds line obtained through 5 generations of self-pollination from a same origin as the sister line indicated above.

This line was selected because of green flesh, non turning, non climacteric long-shelf life, very high sugars very crispy watermelon texture and sutures.

Three cycles of self-pollination from this cross progenies were carried out. The selection and fixation on the self-pollination progenies was made with analytical data for pH, sugars and organic acid contents (Table 8C-E).

2. Selected plants from progeny generated above were crossed with YUSOL.3 a proprietary Syngenta Seeds line described above. This line was selected because of green flesh, shorter cycle, very high sugars, yellow rind and sutures.

Five cycles of self-pollination from the previous cross progenies was made. Selection and fixation breeding process concentrated on the self-pollination progenies for short cycle, green flesh, crispy watermelon texture and yellow rind. Selection and fixation was assisted with analytical data for pH, sugars and organic acid contents. There were so selected and fixed lines progeny YUSAZ A.

3. YUSAZ A lines were used as males pollinators for crosses with three proprietary Syngenta Seeds lines, YUSOL 1 a proprietary Syngenta Seeds line described above. The F1 combination: YUSOL 1/YUSAZ A was obtained.

The analysis of these selected plants is shown in Table 11. The plants were grown under the conditions described in Example 6. The number of fruits tested in each experiment is shown (nr. Frt). The measurements were carried out as described in Example 1-5. The figures for sucrose (suc), hexoses (hex), and total sugars are in g per 100 g fresh weight (fwt). The figures for citric acid and malic acid are in mg per 100 g fresh weight (fwt).

TABLE 11A

YUSAZ A

|  | Growing conditions | Nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| YUSAZ A/1 | SP03PS | 16 | 3.01 | 1.28 | 5.36 | 0.67 | 8.37 |  | 1.78 | 4.6 | 0.2 | 602 | 90 | 28 | 22 | 13 |
|  | FA02PS | 3 | 2.05 | 0.43 | 5.62 | 0.37 | 7.67 |  | 2.74 | 4.6 | 0.1 | 655 | 135 | 21 | 31 | 1 |
|  | SU03PS | 6 | 3.70 | 1.00 | 5.76 | 0.53 | 9.46 | 1.92 | 1.55 | 4.6 | 0.2 | 514 | 115 | 23 | 23 | 18 |
|  | FA03PS | 43 | 2.10 | 0.73 | 7.01 | 0.44 | 9.11 | 1.25 | 3.34 | 4.6 | 0.2 | 558 | 82 | 44 | 13 | 18 |
| Average |  | 68 | 2.72 |  | 5.94 |  | 8.65 |  | 2.35 | 4.6 |  | 582 |  | 29 | 22 |  |
| YUSAZ A/2 | SP03PS | 25 | 3.81 | 0.99 | 5.03 | 0.54 | 8.84 |  | 1.32 | 4.8 | 0.2 | 586 | 55 | 17 | 35 | 14 |
|  | FA02PS | 6 | 3.53 | 0.83 | 5.74 | 0.38 | 9.27 |  | 1.63 | 4.6 | 0.1 | 582 | 70 | 10 | 56 | 15 |
|  | SU03PS | 95 | 3.99 | 1.42 | 4.82 | 0.41 | 8.80 | 1.72 | 1.21 | 4.8 | 0.3 | 543 | 80 | 16 | 33 | 19 |
|  | FA03PS | 52 | 3.70 | 1.30 | 6.12 | 0.35 | 9.81 | 1.28 | 1.66 | 4.7 | 0.1 | 578 | 63 | 18 | 33 | 13 |
| Average |  | 178 | 3.76 |  | 5.43 |  | 9.18 |  | 1.46 | 4.7 |  | 572 |  | 15 | 39 |  |
| average YUSAZ A/1, /2 |  | 246 | 3.24 |  | 5.68 |  | 8.92 |  | 1.90 | 4.7 |  | 577 |  | 19 | 31 |  |

TABLE 11B

F1 Hybrids using YUSAZ A

|  | Growing conditions | Nr frt | suc avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| F1 Hybrid YUSAZ A1/ YUSOL | SP03PS | 12 | 5.24 | 1.83 | 5.09 | 0.99 | 10.33 |  | 0.97 | 4.9 | 0.2 | 659 | 113 | 69 | 10 | 7 |
| F1 Hybrid YUSAZ A2/ YUSOL | SP03PS | 5 | 3.68 | 0.46 | 5.40 | 0.63 | 9.08 |  | 1.47 | 4.6 | 0.1 | 724 | 87 | 35 | 21 | 8 |
| Average |  | 17 | 4.46 |  | 5.24 |  | 9.70 |  | 1.22 | 4.8 |  | 692 |  | 46 | 15 |  |

Characteristics of line YUSAZ A are shown. YUSAZ A/1 and YUSAZ A/2 represent two sister lines. The F1 hybrids result from a cross with line YUSOL.

Example 10

Trait Introgresion into YUSAZ B

The Low pH trait was introgressed in green flesh non climacteric LSL melons with round shape and yellow sutured skin.

1. Selected plants of cross SN80GLIND-103×IOTYU progeny indicated above were back-crossed again with IOTYU, non turning and very low climacteric, green flesh melon (see Table 8D).

Selected plants of the progeny from previous cross were crossed with YUCA-40 a proprietary Syngenta Seeds line obtained through 5 generations of self-pollination from a same origin as the sister line indicated above (see Table 8E).

This line was selected because of green flesh, non climacteric long-shelf life, very high sugars very crispy watermelon texture and sutures.

2. Selected plants from progeny generated after one cycle of self-pollination from the one before were crossed with YUSOL.3 a proprietary Syngenta Seeds line described above. This line was selected because of green flesh, shorter cycle, very high sugars, yellow rind and sutures (see Table 8F).

Five cycles of self-pollination from the previous cross progenies were carried out. Self-pollination progenies were selected for green flesh, crispy watermelon texture, high citric acid content and yellow rind.

3. The selection and fixation was assisted with analytical data for pH, sugars and organic acid contents. Fixed lines progeny YUSAZ B were selected (Table 12).

YUSAZ B is an example of a "Citric+" melon plant.

YUSAZ B lines were used as males pollinators for crosses with three proprietary Syngenta Seeds lines, YUSOL 1 a proprietary Syngenta Seeds line described above. The F1 combination: YUSOL 1/YUSAZ B was obtained (Table 12).

The plants were grown under the conditions described in Example 6. The number of fruits tested in each experiment is shown (nr. Frt). The measurements were carried out as described in Example 1-5. The figures for sucrose (suc), hexoses (hex), and total sugars are in g per 100 g fresh weight (fwt). The figures for citric acid and malic acid are in mg per 100 g fresh weight (fwt).

hybrid MEHARI (Syngenta Seeds) into two low pH versions, one with higher citric acid content and one with lower citric acid content.

1. Direct backcrosses from lines 755YUCIND-49 and 755YUCIND-75 were conducted using as recurrent parent line L53, a proprietary Syngenta Seeds. L53 is a Charentais melon type selected for the purpose because of high sugars, low citric content. L53 is a parent of the commercial hybrid MEHARI (see Table 8F).

During the backcross process and within the progeny of each cross plants with low pH and more or less acid perception (higher or lower citric content) were selected, in addition to other traits to be closer to the recurrent L53.

After the second back-cross (third cross) the following progenies were obtained:

a) L53)3)×755YUCIND75-15/03/06/, selected for low pH and low citric acid content
b) L53)3+)×755YUCIND49-8/2/03/05/, selected for low pH and high citric acid content.

Four cycles of self-pollination from these cross progenies and one further back-cross with L53 were carried out. The selection and fixation breeding process on the self-pollination progenies was assisted with analytical data for pH, sugars and organic acid contents.

2. Fixed lines progenies were selected:

A) L53AZ A selected from previous population a) and fixed for low citric acid content and low pH and, for other traits, close to the recurrent L53.
Line L53AZ A is an example of a "Citric-" melon plant.
B) L53AZ B selected from previous population b) and fixed for low pH and high citric acid content and, for other traits, close to the recurrent L53.

Plants were also selected for intense orange flesh color in presence of the low pH trait. The intensity of the orange color in the flesh had to be particularly selected for, as a generally poor orange color intensity tended to be associated within low pH acid in the fruit flesh (see Table 4).

Progenies lines L53AZ A and L53AZ B, and line L53 were used in crosses with the other parent line of MEHARI to obtain MEHARI AZ A, MEHARI AZ B and MEHARI the current commercial F1, respectively.

TABLE 12

YUSAZ B

| | Growing conditions | nr frt | sucr avg | suc stdev | hex avg | hex stdev | tot. sugar avg | tot. sugar stdev | hex/suc inv activity | pH avg | pH stdev | citric avg | citric stdev | citric/ malic | malic avg | malic stdev |
|---|---|---|---|---|---|---|---|---|---|---|---|---|---|---|---|---|
| YUSAZ B/0 | SP03PS | 7 | 3.16 | 0.66 | 4.99 | 0.60 | 8.14 | | 1.58 | 4.7 | 0.1 | 891 | 73 | 17 | 73 | 12 |
| | FA02PS | 2 | 2.46 | 0.01 | 5.75 | 0.42 | 8.20 | | 2.34 | 4.3 | 0.0 | 848 | 14 | 11 | 75 | 2 |
| | FA03PS | 6 | 1.61 | 0.61 | 6.63 | 0.39 | 8.24 | 1.02 | 4.12 | 4.4 | 0.1 | 878 | 169 | 11 | 78 | 57 |
| Average | | 15 | 2.41 | | 5.79 | | 8.19 | | 2.68 | 4.5 | | 872 | | 13 | 75 | |
| YUSAZ B/1 | SP03PS | 6 | 1.81 | 1.20 | 6.74 | 0.40 | 8.55 | | 3.71 | 4.7 | 0.2 | 696 | 133 | 39 | 18 | 17 |
| | FA02PS | 1 | 2.72 | | 6.76 | | 9.48 | | 2.48 | 4.7 | | 739 | | 18 | 41 | |
| | FA03PS | 8 | 1.21 | 0.45 | 8.39 | 0.20 | 9.60 | 0.69 | 6.94 | 4.7 | 0.1 | 939 | 37 | 26 | 36 | 16 |
| Average | | 15 | 1.91 | | 7.30 | | 9.21 | | 4.38 | 4.7 | | 791 | | 28 | 32 | |
| average YUSAZ B/0, /1 | | 30 | 2.16 | | 6.54 | | 8.70 | | 3.53 | 4.6 | | 832 | | 16 | 53 | |

Characteristics of line YUSAZ B are shown. YUSAZ B/1 and YUSAZ B/2 represent two sister lines. The F1 hybrids result from a cross with line YUSOL.

Example 11

Trait Introgresion to MEHARI F1

The low pH trait was introgressed in orange flesh melons. The selected target was the conversion of the commercial All these products, lines and crosses were tested in agronomic trials and analytical data were collected from fruits (Table 13).

The plants were grown under the conditions described in Example 6. The number of fruits tested in each experiment is shown (nr. Frt). The measurements were carried out as described in Example 1-5. The figures for sucrose (suc), hexoses (hex), and total sugars are in g per 100 g fresh weight (fwt). The figures for citric acid and malic acid are in mg per 100 g fresh weight (fwt).

TABLE 13A

MEHARI, low pH/high pH

|  | Growing conditions | nr frt | suc avg | Suc Stdev | Hex Avg | hex stdev | tot. sugar avg | tot. sugar stdev | Hex/suc inv activity | pH avg | pH stdev | citric avg | citric stdev | citric/ malic | Malic avg | malic stdev |
|---|---|---|---|---|---|---|---|---|---|---|---|---|---|---|---|---|
| Male high pH cit/—(L53) | FA02PS | 4 | 4.11 | 1.66 | 2.93 | 0.67 | 7.04 |  | 0.71 | 6.9 | 0.2 | 65 | 26 | 1 | 114 | 38 |
|  | SP03PS | 3 | 1.98 | 0.85 | 2.70 | 2.05 | 4.68 |  | 1.36 | 6.2 | 0 | 52 | 11 | 1 | 55 | 26 |
|  | FA03PS | 6 | 9.07 | 0.67 | 4.07 | 0.40 | 13.14 | 1.06 | 0.45 | 6.9 | 0.2 | 159 | 40 | 1 | 109 | 18 |
| Average/High pH– |  | 10 | 5.05 |  | 3.23 |  | 8.29 |  |  | 6.7 |  | 92 |  | 1 | 93 |  |
| Male acid cit/— (L53AZ A) | SP03PS | 4 | 2.75 | 1.65 | 3.85 | 0.38 | 6.61 |  | 1.40 | 5.0 | 0.3 | 442 | 168 | 4 | 109 | 51 |
|  | SU03PS | 24 | 2.03 | 1.40 | 3.35 | 1.11 | 5.82 | 1.83 | 1.65 | 4.8 | 0.3 | 484 | 132 | 3 | 150 | 64 |
|  | FA03PS | 48 | 2.76 | 1.85 | 6.07 | 0.62 | 8.82 | 2.19 | 2.20 | 4.8 | 0.4 | 600 | 158 | 3 | 200 | 130 |
| Average/low pH, citric– |  | 76 | 2.51 |  | 4.42 |  | 7.09 |  |  | 4.9 |  | 509 |  | 3 | 153 |  |
| Male acid (L53AZ B) | SP03PS | 3 | 4.82 | 1.37 | 2.72 | 0.30 | 7.54 |  | 0.56 | 5.0 | 0.1 | 654 | 86 | 9 | 75 | 23 |
|  | SU03PS | 12 | 3.74 | 1.50 | 3.33 | 0.89 | 7.08 | 1.64 | 0.89 | 4.7 | 0.1 | 670 | 95 | 10 | 64 | 26 |
|  | FA03PS | 37 | 4.14 | 1.64 | 5.57 | 0.70 | 9.71 | 1.76 | 1.35 | 4.7 | 0.2 | 779 | 74 | 12 | 63 | 20 |
| Average/low pH, citric+ |  | 52 | 4.24 |  | 3.87 |  | 8.11 |  |  | 4.8 |  | 701 |  | 11 | 67 |  |

TABLE 13B

Hybrids of MEHARI, low pH/high pH

|  | Growing conditions | nr frt | suc avg | Suc Stdev | hex avg | hex stdev | Tot. Sugar Avg | tot. sugar stdev | Hex/suc Inv activity | pH avg | pH stdev | citric avg | citric stdev | citric/ malic | malic avg | malic stdev |
|---|---|---|---|---|---|---|---|---|---|---|---|---|---|---|---|---|
| F1 Hybrid MEHARI High pH | SP03PS | 7 | 5.06 | 1.26 | 3.15 | 0.69 | 8.21 |  | 0.62 | 6.6 | 0.2 | 233 | 70 | 3 | 73 | 10 |
|  | FA03PS | 7 | 2.86 | 0.80 | 6.53 | 1.42 | 9.40 | 1.70 | 2.28 | 6.0 | 0.2 | 316 | 137 | 9 | 34 | 23 |
| Average |  | 14 | 3.96 |  | 4.84 |  | 8.80 |  | 1.22 | 6.3 |  | 274 |  | 5 | 54 |  |
| F1 Hybrid low pH, citric– | SP03PS | 7 | 3.10 | 1.42 | 4.46 | 0.53 | 7.55 |  | 1.44 | 5.4 | 0.2 | 447 | 85 | 6 | 79 | 22 |
|  | FA03PS | 6 | 1.39 | 1.46 | 5.75 | 0.66 | 7.14 | 1.99 | 4.14 | 4.6 | 0.2 | 527 | 80 | 7 | 76 | 27 |
| Average |  | 13 | 2.24 |  | 5.10 |  | 7.34 |  | 2.27 | 5.0 |  | 487 |  | 6 | 78 |  |
| F1 Hybrid Low pH, citric+ | SP03PS | 7 | 3.19 | 1.22 | 4.56 | 0.67 | 7.76 |  | 1.43 | 4.8 | 0.1 | 619 | 78 | 12 | 53 | 23 |
|  | SP03OF1 | 3 | 5.82 | 1.55 | 3.63 | 0.76 | 9.45 | 0.86 | 0.62 | 4.9 | 0.2 | 718 | 57 | 20 | 37 | 7 |
|  | FA03PS | 7 | 1.12 | 0.52 | 6.73 | 0.56 | 7.84 | 0.88 | 6.02 | 4.5 | 0.1 | 654 | 128 | 7 | 92 | 69 |
| Average |  | 17 | 3.37 |  | 4.97 |  | 8.35 |  | 1.47 | 4.76 |  | 663 |  | 11 | 60 |  |

Example 12

Sensory Analysis

Sensory analysis of fruits of plants of the instant invention was performed by an Expert panel. The panel was composed of 12 persons, especially trained to describe melons texture, sugar and acid savours. Six sessions of training were carried out before the expert sessions. The training program of the study was:

Training 1: Reading of the lexicon of tasting. Notation of 6 products in the assembly room and discussion in order to see which descriptor is difficult to agree about.

Training 2: Notation of 2 products+2 repeated in laboratory of sensory analysis to see how the panel evaluate the descriptors personally.

Training 3: Results of the training 2 are presented to the panel. Notation of 2 products+2 repeated in the assembly room and discussion. Notation of 2 products in the individual cabins.

Training 4: Works on sugar and acid solutions at different concentrations to evaluate the difficulties of the panel on these descriptors. Results of the training 3 are presented to the panel. Notation of 3 products+1 repeated in the assembly room and discussion. Notation of 3 products+1 repeated in individual cabins.

Training 5. Notation of 4 products in the assembly room and notation of 2 products+2 repeated in the individual cabins. It allows us to check the repeatability of the tasters inside the session. Works on acid solutions.

Training 6: Notation of 3 products in the assembly room and notation of 2 products+2 repeated in the individual cabins to check the repeatability of the tasters inside the session.

The sensory analysis was carried out in an air-conditioned sensory analysis laboratory equipped with individual cabins. A structured scale of quotation in 10 points (from 0 to 9) was used with the following descriptors:

Sweet Savor
Definition: It is about the perception of the sweet savour perceived in mouth. Mode of evaluation: Chew the product until its disappearance. Estimate the intensity of the sweet savour. Notation: 0=not sweet, 9=very sweet Acid Savor
Definition: It is about the perception of the acid savour perceived in mouth. Mode of evaluation: Chew the product until its disappearance. Estimate the intensity of the acid savour. Notation: 0=not acid, 9=very acid.

Protocol of Preparation
Wash of melons in the cold water
Longitudinal cutting of the melon
Removing of the pulp and the seeds
Cutting each half of melons in 3 parts (longitudinal cutting)
Removing of the extremities of 3 parts
Cutting each part in 2 in order to have 6 parts on the half of the melon Presentation of the Products Samples are presented coded with random numbers and according to a plan of presentation (Latin Square) avoiding the effects of presentation order.

The products are given one after the other.

Tables 14 and 15 show the results of two sensory analysis conducted on different fruits.

In Table 14, plants were sown in early March and transplanted to open protected fields as vine crops in early April. Fruits were harvested in early July. In Table 14 A, fruits were stored for 7 to 12 days at 10° C. followed by 2 days at 20° C. In Table 14 B, fruits were stored for 4 to 8 days at 10° C. followed by 2 days at 20° C.

In Table 15, plants were sown in early August and transplanted to plastic houses as staked crops in late August. Fruits were harvested in early November. Fruits were stored for 4 to 8 days 5° C. followed by 3 days at 20° C.

Sensory analysis was performed on the number of fruits indicated in the Tables. Each fruit was tested by the 12 qualified tasters. The figures for acid and sugar savors for each line represent the average of the number of fruit times 12 (for the 12 tasters). Tables 14 and 15 also show measurements of the pH and contents of sugars and organic acid for the fruits tested.

TABLE 14A

|  |  | FRT nr | Brix | pH | GLU g/100 g | SUC g/100 g | FRU g/100 g | Tot sug g/100 g | Citric Ac mg/100 g | Malic Ac mg/100 g | ACID savor | SUGAR savor |
|---|---|---|---|---|---|---|---|---|---|---|---|---|
| YUSOL/1 X | Avg | 10 | 11.7 | 6.24 | 1.2 | 7.2 | 2.1 | 10.6 | 309 | 4 | 0.5 | 5.6 |
| SOLAZ/1 basic | Std Dev |  | 2.1 | 0.30 | 0.3 | 2.3 | 0.3 | 1.9 | 121 | 10 | 0.3 | 1.0 |
| YUSAZ A | Avg | 6 | 12.7 | 4.79 | 1.1 | 7.7 | 2.0 | 10.7 | 808 | 0 | 2.1 | 5.4 |
| X YUSOL | Std Dev |  | 0.5 | 0.09 | 0.2 | 0.6 | 0.2 | 0.5 | 17 | 0 | 0.7 | 0.5 |
| SOLAZ/2 | Avg | 10 | 13.5 | 4.68 | 1.5 | 7.9 | 2.0 | 11.3 | 832 | 18 | 3.6 | 4.7 |
| X YUSOL/3 | Std Dev |  | 1.4 | 0.17 | 0.5 | 1.0 | 0.3 | 1.0 | 37 | 20 | 0.5 | 0.3 |
| SOLAZ/1 | Avg | 10 | 13.2 | 4.58 | 1.8 | 7.2 | 2.4 | 11.4 | 816 | 41 | 3.1 | 4.7 |
| X YUSOL/1 | Std Dev |  | 0.8 | 0.22 | 0.6 | 1.2 | 0.4 | 0.6 | 37 | 32 | 1.2 | 0.6 |
| Average SOLAZ X YUSOL |  | 20 | 13.4 | 4.63 | 1.7 | 7.6 | 2.2 | 11.4 | 824 | 30 | 3.4 | 4.7 |

TABLE 14B

|  |  | FRT nr | Brix | pH | GLU g/100 g | SUC g/100 g | FRU g/100 g | SUG Tot | Citric Ac mg/100 g | Malic mg/100 g | ACID savor | SUGAR savor |
|---|---|---|---|---|---|---|---|---|---|---|---|---|
| Female Mehari | Avg | 6 | 13.2 | 6.64 | 1.0 | 8.5 | 1.7 | 11.2 | 272 | 63 | 0.5 | 5.8 |
| X L53 | Std Dev |  | 1.7 | 0.09 | 0.1 | 1.5 | 0.2 | 1.5 | 54 | 32 | 0.2 | 0.6 |
| Female Mehari | Avg | 7 | 13.4 | 5.20 | 1.1 | 7.8 | 1.9 | 10.8 | 652 | 88 | 1.7 | 5.2 |
| X L53 AZ A/1 | Std Dev |  | 0.7 | 0.11 | 0.2 | 0.8 | 0.3 | 0.9 | 87 | 69 | 0.4 | 0.4 |
| Female Mehari | Avg | 5 | 13.1 | 5.28 | 1.2 | 8.1 | 2.0 | 11.3 | 581 | 107 | 1.6 | 5.3 |
| X L53 AZ A/2 | Std Dev |  | 0.8 | 0.08 | 0.2 | 0.9 | 0.1 | 0.8 | 50 | 40 | 0.4 | 0.6 |
| AVG Female Mehari X L53 AZ A |  | 12 | 13.3 | 5.24 | 1.2 | 8.0 | 2.0 | 11.1 | 617 | 98 | 1.7 | 5.3 |
| Female Mehari | Avg | 6 | 12.2 | 4.98 | 1.2 | 7.1 | 1.9 | 10.2 | 708 | 107 | 3.2 | 4.6 |
| X L53 AZ B | Std Dev |  | 1.0 | 0.21 | 0.1 | 0.7 | 0.2 | 0.9 | 78 | 44 | 0.6 | 0.3 |

TABLE 15

|  |  | FRT nr | Brix | pH | GLU g/100 g | SUC g/100 g | FRU g/100 g | Tot sug g/100 g | Citric Ac mg/100 g | Malic Ac mg/100 g | ACID savor | SUGAR savor |
|---|---|---|---|---|---|---|---|---|---|---|---|---|
| SOLAZ/2 | Avg | 3 | 9.60 | 4.53 | 1.97 | 2.98 | 2.47 | 7.41 | 717 | 0 | 3.78 | 4.31 |
| X YUSOL/3 | Std Dev |  | 0.53 | 0.06 | 0.36 | 0.30 | 0.36 | 0.94 | 39 | 0 | 0.84 | 0.55 |
| SOLAZ/1 | Avg | 2 | 11.00 | 4.74 | 2.14 | 4.04 | 3.05 | 9.24 | 574 | 0 | 2.54 | 5.63 |
| X YUSOL/1 | Std Dev |  | 0.85 | 0.09 | 0.35 | 0.00 | 0.09 | 0.44 | 169 | 0 | 1.20 | 0.06 |
| Average SOLAZ X YUSOL |  | 5 | 10.2 | 4.6 | 2.0 | 3.4 | 2.7 | 8.1 | 660 | 0 | 3.3 | 4.8 |
| YUSOL X | Avg | 5 | 12.40 | 4.71 | 3.04 | 4.02 | 3.59 | 10.65 | 713 | 18 | 2.95 | 5.47 |
| YUSAZ A | Std Dev |  | 1.04 | 0.17 | 0.56 | 1.04 | 0.67 | 0.68 | 42 | 15 | 0.40 | 0.75 |
| TD X L53 | Avg | 8 | 12.13 | 4.97 | 1.23 | 5.53 | 2.06 | 8.82 | 696 | 74 | 2.56 | 5.72 |
| AZ/A | Std Dev |  | 1.13 | 0.14 | 0.36 | 1.13 | 0.32 | 0.80 | 83 | 41 | 0.85 | 0.39 |
| Mehari female | Avg | 3 | 9.50 | 5.10 | 1.48 | 3.48 | 2.52 | 7.48 | 632 | 62 | 2.17 | 5.50 |
| X L53 AZ/A | Std Dev |  | 1.32 | 0.27 | 0.17 | 0.70 | 0.37 | 1.17 | 79 | 25 | 0.43 | 0.55 |

Example 13

Molecular Marker Analysis

DNA was extracted from young leaves (15 day-old seedlings). Leaves were freeze-dried and DNA was extracted following the method of Dellaporta (Dellaporta 1983).

PCR cycling conditions were: 15 s denaturation at 94° C. followed by 15 s annealing at 54° C. and 30 s extension at 72° C. for 40 cycles. Sample's DNA was initially denatured for 2 minutes at 94° C. and extended for 2 min at 72° C. after PCR.

The PCR mix contained 1.65 mM $MgCl_2$, 60 mM of each deoxyribonucleotide, 1×Taq Buffer, 0.2 unit Taq polymerase, 15-20 ng template DNA and 400 nM of each non-fluorescent primer or 200 nM of each fluorescently labeled primer. Fluorescent primers were labeled with 6-FAM, NED or HEX. Fluorescent PCR products were separated on an ABI3700 capillary sequencer and their sizes measured using Applied Biosystem's Genescan and Genotyper fragment analysis software.

Non-fluorescent PCR products were separated by electrophoresis in 3% agarose gels (Resophor, Eurobio) at 400V with cooling system. Gels were stained with ethidium bromide. Three markers were used, CMAT141 (described in Danin-Poleg et al. (2001) Theor. Appl. Genet. 102: 61-72 and Danin-Poleg et al. (2002) Euphytica 125: 373-384) and NE0585 and NE1746. The primers for these markers are shown below.

|  | Forward Primer (5'-3') | Reverse Primer (5'-3') |
|---|---|---|
| CMAT141 | AAGCACACCACCACCCGTAA (SEQ ID NO: 1) | GTGAATGGTATGTTATCCTTG (SEQ ID NO: 2) |
| NE0585 | GTATCATGTCGGAGAAACG (SEQ ID NO: 3) | CCTTTATCCCCACTTTTTC (SEQ ID NO: 4) |
| NE1746 | TTCTCCGATGTGTCCTCTC (SEQ ID NO: 5) | GTCGCTTGGAATATATCGG (SEQ ID NO: 6) |

Example 14

Analysis of Accessions

A number of melon accessions comprising a low pH trait were analyzed using the markers above. The sizes of the amplified fragments are reported in Table 16 below. The indicated sizes (in bp) are not absolute but relative to the other size products detected with the same primer pair. The real (exact) size of the amplified fragments (e.g. determined by sequencing) could be slightly different (+/−1 bp) of those indicated herein.

TABLE 16

| | CMAT141 | | NE0585 | | | NE1746 | | |
|---|---|---|---|---|---|---|---|---|
| IND35-1.2. | 173 | | 230 | | | 127 | | |
| IND35-2.3. | 168 | | | | 232 | | 124 | |
| FAGOUS2:4- | | 176 | 228 | | | 253 | 121 | |
| FAGOUS2:5- | | 176 | | | | | 121 | 142 |
| FAGOUS2:7- | | 176 | | | | 253 | | 142 |
| PI414723 | | 175 | 228 | | | | 124 | |
| PI414724 | | 175 | | | | | 124 | |
| PI161375 | | 175 | 228 | | | | 124 | |
| PI124112 | | 175 | | | 239 | | 124 | |

Example 15

Evolution of Fruit Characteristics of Fruits Kept on the Plant

Plants were grown as for the plants in Table 15 above. Fruits were harvested at different maturation times points (cycle) calculated by the difference between the harvest date (HDT) and the pollination date (PDT). Maturity was considered as reached at a particular time point in the cycle, when the average of the sucrose content for fruits at the particular time point in the cycle reached 2.0 g sucrose per 100 g fwt and using other ripening signs such as side leaf senescence. The results are shown in Table 17.

The results are based on individual fruit measurements and it is understood that some fruits may yield deviating values because of damages, aberrant development or other environmental factors.

TABLE 17

| | FRT nr | PDT | HDT | Cycle | Flesh Orange Colour 1 to 5 | pH | Brix | GLU g/100 g | SUC g/100 g | FRU g/100 g | HEX g/100 g | Tot sug g/100 g | Citric Ac mg/100 g | Malic Ac mg/100 g |
|---|---|---|---|---|---|---|---|---|---|---|---|---|---|---|
| TD X | 1 | 17 | 37 | 20 | 1 | 5.09 | 5.0 | 1.6 | 0.0 | 1.4 | 2.6 | 3.0 | 169 | 460 |
| L53 AZ A/1 | 1 | 16 | 37 | 21 | 1 | 4.83 | 5.4 | 1.8 | 0.0 | 1.7 | 3.9 | 3.5 | 167 | 273 |

TABLE 17-continued

| | | | | | | | GLU | SUC | FRU | HEX | Tot sug | Citric Ac | Malic Ac |
|---|---|---|---|---|---|---|---|---|---|---|---|---|---|
| Maturity reached between cycle 33 and 40 | 1 | 14 | 37 | 23 | 1 | 4.94 | 4.6 | 1.4 | 0.0 | 1.4 | 2.7 | 2.8 | 128 | 243 |
| | 1 | 16 | 40 | 24 | 1 | 4.55 | 4.8 | 1.4 | 0.0 | 1.2 | 2.8 | 2.6 | 387 | 314 |
| | 1 | 16 | 40 | 24 | 1 | 4.66 | 5.0 | 1.2 | 0.0 | 1.7 | 2.9 | 2.9 | 387 | 114 |
| | 1 | 14 | 40 | 26 | 2 | 4.88 | 6.5 | 1.9 | 0.0 | 1.4 | 2.3 | 3.3 | 498 | 255 |
| | 1 | 14 | 40 | 26 | 2 | 4.44 | 7.0 | 1.4 | 0.6 | 2.7 | 4.1 | 4.7 | 852 | 119 |
| | 1 | 14 | 44 | 30 | 2 | 4.36 | 6.7 | 2.3 | 0.4 | 2.0 | 3.2 | 4.6 | 776 | 178 |
| | 1 | 14 | 44 | 30 | 2 | 4.47 | 7.0 | 1.7 | 0.5 | 2.2 | 3.9 | 4.3 | 528 | 77 |
| | 1 | 14 | 44 | 30 | 2 | 4.70 | 7.0 | 2.3 | 0.2 | 2.4 | 4.7 | 5.0 | 649 | 11 |
| | 1 | 14 | 47 | 33 | 2 | 4.37 | 6.5 | 2.0 | 0.0 | 1.6 | 3.2 | 3.6 | 730 | 174 |
| | 1 | 14 | 47 | 33 | 2 | 4.59 | 7.0 | 1.2 | 1.0 | 1.7 | 2.9 | 3.9 | 453 | 117 |
| | 1 | 14 | 47 | 33 | 3 | 4.85 | 13.6 | 2.3 | 3.9 | 1.9 | 4.0 | 8.2 | 876 | 199 |
| | 1 | 14 | 54 | 40 | 3 | 5.02 | 13.0 | 1.0 | 7.3 | 2.2 | 3.2 | 10.5 | 663 | 89 |
| | 1 | 17 | 57 | 40 | 3 | 4.83 | 11.5 | 1.5 | 4.5 | 2.4 | 3.9 | 8.4 | 590 | 155 |
| | 1 | 16 | 57 | 41 | 3 | 4.79 | 14.0 | 1.8 | 6.9 | 2.1 | 3.9 | 10.9 | 890 | 31 |
| | 1 | 16 | 58 | 42 | 4 | 4.75 | 13.3 | 2.1 | 5.2 | 2.0 | 3.1 | 9.2 | 985 | 104 |
| | 1 | 14 | 57 | 43 | 3 | 4.96 | 12.7 | 1.7 | 5.5 | 1.9 | 4.3 | 9.0 | 893 | 167 |
| | 1 | 14 | 57 | 43 | 4 | 5.24 | 14.0 | 1.4 | 8.4 | 2.3 | 3.7 | 12.1 | 648 | 40 |
| | 1 | 14 | 57 | 43 | 4 | 5.06 | 12.5 | 1.0 | 5.9 | 1.8 | 2.8 | 8.7 | 623 | 48 |
| | 1 | 14 | 57 | 43 | 4 | 5.00 | 12.5 | 1.3 | 5.7 | 2.2 | 3.4 | 9.2 | 758 | 29 |
| TD X L53 AZ A/2 Maturity reached between cycle 34 and 38 | 1 | 17 | 37 | 20 | 1 | 4.45 | 4.8 | 1.7 | 0.1 | 1.8 | 3.5 | 3.5 | 307 | 319 |
| | 1 | 17 | 37 | 20 | 1 | 4.53 | 5.2 | 1.9 | 0.0 | 2.0 | 5.0 | 3.9 | 331 | 332 |
| | 1 | 14 | 37 | 23 | 1 | 4.43 | 4.1 | 1.0 | 0.0 | 1.1 | 2.3 | 2.1 | 572 | 323 |
| | 1 | 17 | 40 | 23 | 3 | 4.55 | 7.0 | 1.3 | 0.8 | 1.7 | 3.0 | 3.8 | 682 | 120 |
| | 1 | 14 | 40 | 26 | 2 | 4.48 | 6.0 | 1.3 | 0.3 | 1.8 | 3.2 | 3.5 | 590 | 136 |
| | 1 | 14 | 40 | 26 | 3 | 4.44 | 6.2 | 1.9 | 0.0 | 1.9 | 1.5 | 3.8 | 594 | 206 |
| | 1 | 17 | 44 | 27 | 2 | 4.36 | 4.9 | 1.5 | 0.0 | 1.3 | 2.8 | 2.9 | 640 | 295 |
| | 1 | 19 | 47 | 28 | 3 | 4.33 | 8.9 | 2.8 | 0.0 | 2.7 | 4.4 | 5.5 | 977 | 156 |
| | 1 | 14 | 44 | 30 | 2 | 4.65 | 6.0 | 1.0 | 1.3 | 2.4 | 3.4 | 4.8 | 715 | 56 |
| | 1 | 17 | 51 | 34 | 3 | 4.43 | 10.1 | 2.9 | 1.0 | 2.9 | 5.9 | 6.8 | 989 | 141 |
| | 1 | 17 | 51 | 34 | 3 | 4.77 | 11.0 | 1.9 | 3.5 | 2.5 | 4.4 | 7.9 | 836 | 31 |
| | 1 | 17 | 51 | 34 | 3 | 4.91 | 10.5 | 1.3 | 5.3 | 1.9 | 3.2 | 8.5 | 753 | 96 |
| | 1 | 16 | 51 | 35 | 3 | 4.31 | 8.6 | 2.2 | 0.9 | 2.1 | 5.0 | 5.3 | 970 | 216 |
| | 1 | 16 | 54 | 38 | 3 | 4.76 | 14.1 | 2.3 | 5.5 | 2.2 | 3.8 | 10.1 | 983 | 164 |
| | 1 | 14 | 54 | 40 | 4 | 4.80 | 14.8 | 2.1 | 7.0 | 2.1 | 4.0 | 11.3 | 992 | 166 |
| | 1 | 14 | 54 | 40 | 4 | 5.03 | 15.0 | 0.8 | 9.0 | 1.8 | 2.6 | 11.6 | 843 | 5 |
| | 1 | 17 | 58 | 41 | 3 | 4.99 | 14.5 | 1.6 | 8.0 | 2.1 | 3.6 | 11.6 | 909 | 75 |
| | 1 | 14 | 57 | 43 | 4 | 4.97 | 12.0 | 0.8 | 5.8 | 1.7 | 2.5 | 8.2 | 635 | 76 |
| | 1 | 14 | 57 | 43 | 5 | 5.20 | 14.0 | 1.2 | 6.3 | 1.7 | 2.9 | 9.2 | 711 | 64 |
| | 1 | 14 | 58 | 44 | 4 | 5.06 | 16.0 | 1.6 | 8.5 | 1.7 | 3.4 | 11.9 | 986 | 50 |

| | FRT nr | PDT | HDT | Cycle | Colour | pH | Brix | GLU g/100 g | SUC g/100 g | FRU g/100 g | HEX g/100 g | Tot sug g/100 g | Citric Ac mg/100 g | Malic Ac mg/100 g |
|---|---|---|---|---|---|---|---|---|---|---|---|---|---|---|
| Female Mehari X L53 AZ A/1 Maturity reached between cycle 36 and 38 | 1 | 21 | 40 | 20 | 1 | 4.45 | 4.7 | 1.5 | 0.0 | 1.3 | 1.3 | | 437 | 292 |
| | 1 | 17 | 37 | 20 | 1 | 4.62 | 4.5 | 1.1 | 0.1 | 1.4 | 2.5 | 2.6 | 295 | 98 |
| | 1 | 17 | 40 | 23 | 1 | 4.78 | 5.0 | 1.0 | 0.2 | 1.9 | 2.9 | 3.1 | 482 | 71 |
| | 1 | 14 | 40 | 26 | 2 | 4.54 | 5.0 | 1.1 | 0.1 | 1.6 | 2.7 | 2.8 | 397 | 81 |
| | 1 | 17 | 44 | 27 | 2 | 4.46 | 5.0 | 1.2 | 0.4 | 1.9 | 3.1 | 3.4 | 547 | 38 |
| | 1 | 17 | 44 | 27 | 2 | 4.43 | 4.9 | 1.6 | 0.0 | 1.4 | 1.4 | 3.0 | 561 | 187 |
| | 1 | 17 | 44 | 27 | 2 | 4.52 | 6.0 | 1.5 | 0.7 | 1.9 | 3.4 | 4.1 | 505 | 18 |
| | 1 | 19 | 51 | 32 | 4 | 4.81 | 8.0 | 1.3 | 2.7 | 2.2 | 3.5 | 6.2 | 575 | 76 |
| | 1 | 19 | 51 | 32 | 2 | 4.50 | 6.2 | 2.0 | 0.0 | 1.6 | 2.8 | 3.6 | 592 | 75 |
| | 1 | 19 | 51 | 32 | 3 | 4.76 | 7.0 | 1.5 | 1.4 | 2.0 | 3.5 | 4.9 | 465 | 105 |
| | 1 | 14 | 50 | 36 | 3 | 5.99 | 8.6 | 1.5 | 2.5 | 1.6 | 2.6 | 5.6 | 414 | 259 |
| | 1 | 16 | 53 | 37 | 5 | 6.28 | 9.0 | 1.4 | 3.0 | 1.8 | 3.3 | 6.3 | 297 | 166 |
| | 1 | 17 | 54 | 37 | 4 | 5.57 | 8.5 | 1.7 | 2.6 | 2.6 | 4.3 | 6.9 | 309 | 261 |
| | 1 | 17 | 54 | 37 | 2 | 5.68 | 8.4 | 1.6 | 1.7 | 1.4 | 2.6 | 4.8 | 339 | 276 |
| | 1 | 14 | 51 | 37 | 3 | 4.86 | 5.8 | 1.3 | 0.4 | 1.4 | 3.9 | 3.1 | 446 | 339 |
| | 1 | 14 | 51 | 37 | 4 | 6.36 | 9.0 | 1.5 | 2.7 | 1.9 | 3.4 | 6.1 | 276 | 167 |
| | 1 | 17 | 54 | 37 | 4 | 5.21 | 12.0 | 1.6 | 4.5 | 1.9 | 3.5 | 8.0 | 532 | 56 |
| | 1 | 16 | 54 | 38 | 5 | 5.79 | 9.5 | 1.4 | 3.8 | 2.7 | 4.1 | 7.9 | 351 | 264 |
| | 1 | 17 | 57 | 40 | 2 | 5.47 | 9.0 | 1.7 | 1.5 | 1.4 | 4.0 | 4.6 | 410 | 312 |
| | 1 | 17 | 57 | 40 | 4 | 4.63 | 10.9 | 2.4 | 3.0 | 2.3 | 3.8 | 7.7 | 894 | 111 |
| | 1 | 17 | 57 | 40 | 5 | 6.22 | 9.5 | 1.5 | 3.8 | 2.1 | 3.6 | 7.4 | 360 | 277 |
| Female Mehari X L53 AZ A/2 Maturity reached between cycle 35 and 37 | 1 | 17 | 37 | 20 | 1 | 4.84 | 4.5 | 0.7 | 0.3 | 1.7 | 2.5 | 2.7 | 368 | 33 |
| | 1 | 17 | 37 | 20 | 1 | 5.25 | 4.7 | 1.6 | 0.0 | 1.5 | 2.5 | 3.1 | 210 | 375 |
| | 1 | 17 | 37 | 20 | 1 | 5.31 | 4.3 | 1.4 | 0.0 | 1.2 | 2.6 | 2.6 | 200 | 288 |
| | 1 | 17 | 44 | 27 | 2 | 4.52 | 4.9 | 1.7 | 0.0 | 1.4 | 2.4 | 3.1 | 320 | 190 |
| | 1 | 17 | 44 | 27 | 2 | 4.49 | 5.0 | 0.8 | 0.3 | 1.7 | 2.5 | 2.8 | 423 | 5 |
| | 1 | 17 | 44 | 27 | 2 | 6.69 | 5.3 | 1.5 | 0.0 | 0.8 | 3.4 | 2.4 | 238 | 160 |
| | 1 | 17 | 44 | 27 | 2 | 4.47 | 6.0 | 2.1 | 0.0 | 1.7 | 7.5 | 3.8 | 437 | 183 |
| | 1 | 21 | 51 | 30 | 3 | 4.63 | 9.5 | 2.6 | 1.4 | 2.4 | 4.3 | 6.4 | 548 | 150 |
| | 1 | 17 | 47 | 30 | 2 | 4.53 | 7.4 | 2.4 | 0.1 | 2.1 | 4.0 | 4.6 | 672 | 126 |
| | 1 | 17 | 47 | 30 | 3 | 4.60 | 6.5 | 1.5 | 1.0 | 2.3 | 3.8 | 4.8 | 562 | 44 |
| | 1 | 17 | 51 | 34 | 2 | 4.68 | 6.5 | 2.0 | 0.2 | 1.9 | 2.6 | 4.1 | 713 | 99 |
| | 1 | 17 | 51 | 34 | 3 | 4.50 | 9.9 | 2.7 | 1.5 | 2.5 | 4.9 | 6.7 | 944 | 118 |
| | 1 | 16 | 51 | 35 | 4 | 5.35 | 10.5 | 1.7 | 4.0 | 2.9 | 4.6 | 8.6 | 723 | 32 |
| | 1 | 16 | 51 | 35 | 4 | 4.77 | 11.7 | 2.2 | 3.2 | 2.2 | 3.7 | 7.6 | 904 | 133 |
| | 1 | 14 | 50 | 36 | 2 | 5.84 | 7.1 | 1.4 | 0.6 | 1.5 | 2.6 | 3.5 | 224 | 168 |
| | 1 | 14 | 50 | 36 | 4 | 6.09 | 7.0 | 1.1 | 2.1 | 2.1 | 3.2 | 5.3 | 273 | 201 |

TABLE 17-continued

| | | | | | | | | | | | | | |
|---|---|---|---|---|---|---|---|---|---|---|---|---|---|
| | 1 | 14 | 50 | 36 | 2 | 5.95 | 8.3 | 1.6 | 1.7 | 1.8 | 3.7 | 5.1 | 279 | 235 |
| | 1 | 14 | 50 | 36 | 5 | 6.51 | 9.5 | 1.7 | 2.9 | 2.7 | 4.4 | 7.3 | 336 | 202 |
| | 1 | 14 | 51 | 37 | 4 | 5.13 | 10.0 | 1.5 | 3.8 | 2.4 | 3.9 | 7.7 | 599 | 77 |
| | 1 | 19 | 57 | 38 | 3 | 5.60 | 13.1 | 2.3 | 4.1 | 2.2 | 3.3 | 8.6 | 613 | 150 |
| | 1 | 19 | 57 | 38 | 3 | 4.62 | 12.2 | 3.0 | 3.7 | 2.7 | 5.2 | 9.4 | 1011 | 63 |

| | FRT nr | PDT | HDT | Cycle | pH | Brix | GLU g/100 g | SUC g/100 g | FRU g/100 g | HEX g/100 g | Tot sug g/100 g | Citric Ac mg/100 g | Malic Ac mg/100 g |
|---|---|---|---|---|---|---|---|---|---|---|---|---|---|
| SOLAZ/2 X YUSOL/3 Maturity reached between cycle 38 and 41 | x2 | 9 | 37 | 28 | 4.23 | 5.0 | 1.6 | 0.1 | 1.7 | 4.0 | 3.3 | 664 | 116 |
| | x2 | 9 | 37 | 28 | 4.30 | 5.1 | 1.8 | 0.0 | 1.9 | 4.8 | 3.7 | 496 | 123 |
| | x2 | 9 | 37 | 28 | 4.21 | 5.9 | 2.4 | 0.0 | 2.0 | 3.7 | 4.4 | 674 | 77 |
| | 1 | 9 | 37 | 28 | 4.53 | 6.0 | 2.3 | 1.0 | 2.6 | 4.8 | 5.9 | 675 | 102 |
| | x2 | 9 | 37 | 28 | 4.19 | 5.3 | 1.6 | 0.1 | 1.8 | 3.9 | 3.5 | 703 | 123 |
| | x2 | 9 | 37 | 28 | 4.37 | 4.6 | 1.4 | 0.0 | 1.4 | 2.9 | 2.8 | 509 | 264 |
| | x2 | 10 | 40 | 30 | 4.18 | 5.5 | 2.0 | 0.0 | 1.9 | 3.2 | 3.9 | 545 | 94 |
| | x2 | 9 | 40 | 31 | 4.21 | 6.4 | 2.1 | 0.0 | 2.1 | 3.5 | 4.1 | 795 | 71 |
| | 1x | 9 | 40 | 31 | 4.25 | 7.2 | 2.9 | 0.0 | 2.9 | 4.8 | 5.8 | 723 | 186 |
| | 1 | 9 | 40 | 31 | 4.37 | 6.8 | 2.3 | 0.3 | 2.8 | 5.1 | 5.4 | 667 | 55 |
| | x2 | 9 | 40 | 31 | 4.15 | 5.5 | 1.9 | 0.0 | 2.0 | 4.7 | 3.9 | 728 | 146 |
| | 1x | 9 | 44 | 35 | 4.21 | 8.6 | 2.8 | 0.0 | 3.3 | 6.4 | 6.2 | 990 | 34 |
| | x2 | 9 | 44 | 35 | 4.70 | 7.0 | 2.1 | 1.7 | 3.0 | 5.0 | 6.7 | 706 | 0 |
| | x2 | 9 | 44 | 35 | 4.18 | 7.3 | 2.3 | 0.0 | 2.8 | 5.3 | 5.1 | 984 | 32 |
| | x2 | 9 | 44 | 35 | 4.17 | 7.3 | 2.1 | 0.0 | 2.7 | 5.8 | 4.8 | 992 | 28 |
| | x2 | 9 | 44 | 35 | 4.06 | 6.5 | 2.3 | 0.0 | 2.3 | 4.9 | 4.6 | 990 | 67 |
| | 1 | 9 | 44 | 35 | 4.34 | 7.2 | 1.9 | 0.5 | 2.3 | 4.2 | 4.7 | 736 | 14 |
| | 1 | 9 | 47 | 38 | 4.49 | 10.2 | 2.4 | 3.3 | 2.8 | 5.2 | 8.5 | 761 | 0 |
| | x2 | 9 | 47 | 38 | 4.24 | 9.0 | 2.6 | 0.6 | 3.1 | 6.7 | 6.2 | 782 | 15 |
| | x2 | 9 | 47 | 38 | 4.21 | 10.5 | 3.1 | 0.9 | 3.4 | 7.3 | 7.5 | 834 | 41 |
| | 1 | 9 | 47 | 38 | 4.60 | 9.2 | 1.7 | 2.7 | 2.5 | 4.2 | 6.9 | 695 | 0 |
| | x2 | 9 | 47 | 38 | 4.21 | 10.3 | 2.9 | 1.2 | 3.0 | 6.2 | 7.1 | 1052 | 53 |
| | x2 | 9 | 50 | 41 | 4.44 | 9.2 | 2.2 | 2.0 | 2.4 | 4.7 | 6.6 | 701 | 24 |
| | x2 | 9 | 50 | 41 | 4.69 | 10.5 | | | | | | 803 | 66 |
| | x2 | 9 | 50 | 41 | 4.76 | 10.2 | | | | | | 853 | 37 |
| | x2 | 9 | 50 | 41 | 4.77 | 10.4 | 1.8 | 3.6 | 2.8 | 4.6 | 8.2 | 637 | 1 |
| | x2 | 9 | 50 | 41 | 4.56 | 12.2 | | | | | | 943 | 0 |
| | 1 | 9 | 50 | 41 | 4.51 | 9.4 | 1.8 | 2.9 | 2.1 | 3.9 | 6.9 | 694 | 0 |
| | x2 | 9 | 51 | 42 | 4.55 | 10.5 | | | | | | 887 | 0 |
| | x2 | 9 | 54 | 45 | 4.28 | 12.4 | 2.7 | 3.3 | 2.6 | 5.0 | 8.7 | 982 | 48 |
| | x2 | 9 | 54 | 45 | 4.23 | 10.8 | 2.4 | 3.0 | 2.6 | 4.7 | 8.0 | 1026 | 61 |
| | 1 | 9 | 54 | 45 | 4.44 | 12.9 | 2.7 | 4.7 | 2.4 | 3.6 | 9.8 | 997 | 52 |
| SOLAZ/1 X YUSOL/1 Maturity reached between cycle 38 and 41 | x2 | 10 | 37 | 27 | 4.36 | 4.8 | 1.7 | 0.0 | 1.7 | 3.7 | 3.3 | 526 | 136 |
| | 1 | 10 | 37 | 27 | 4.84 | 4.0 | 1.4 | 0.4 | 2.1 | 3.5 | 3.9 | 428 | 27 |
| | 1 | 9 | 37 | 28 | 4.51 | 4.5 | 2.1 | 0.0 | 2.1 | 4.2 | 4.2 | 476 | 86 |
| | 1 | 9 | 37 | 28 | 4.49 | 5.4 | 2.1 | 1.1 | 2.4 | 4.5 | 5.6 | 524 | 55 |
| | 1 | 9 | 40 | 31 | 4.42 | 6.2 | 1.8 | 0.4 | 2.8 | 4.6 | 5.1 | 598 | 62 |
| | 1 | 9 | 40 | 31 | 4.38 | 5.0 | 1.6 | 0.1 | 2.0 | 3.6 | 3.7 | 546 | 94 |
| | 1 | 9 | 40 | 31 | 4.25 | 5.8 | 1.9 | 0.0 | 2.1 | 3.6 | 3.9 | 642 | 91 |
| | 1 | 9 | 44 | 35 | 4.53 | 7.0 | 2.2 | 1.6 | 3.2 | 5.4 | 7.0 | 654 | 0 |
| | 1 | 9 | 44 | 35 | 4.24 | 8.7 | 2.7 | 0.5 | 3.0 | 5.3 | 6.1 | 977 | 70 |
| | 1 | 9 | 44 | 35 | 4.44 | 7.6 | 2.0 | 0.8 | 2.6 | 4.6 | 5.4 | 498 | 0 |
| | 1 | 9 | 44 | 35 | 4.38 | 8.6 | 2.3 | 1.4 | 3.1 | 5.5 | 6.9 | 640 | 6 |
| | 1 | 9 | 47 | 38 | 4.42 | 10.4 | 1.8 | 2.4 | 2.6 | 4.4 | 6.9 | 733 | 0 |
| | 1 | 9 | 47 | 38 | 4.53 | 8.0 | 2.0 | 1.8 | 3.0 | 4.9 | 6.7 | 540 | 0 |
| | 1 | 9 | 47 | 38 | 4.74 | 8.5 | 2.2 | 1.6 | 2.7 | 5.4 | 6.5 | 600 | 3 |
| | 1 | 9 | 47 | 38 | 4.50 | 10.1 | 2.3 | 1.8 | 2.5 | 3.4 | 6.7 | 568 | 15 |
| | 1 | 9 | 50 | 41 | 4.45 | 10.2 | 1.7 | 2.6 | 2.2 | 4.0 | 6.6 | 676 | 8 |
| | 1 | 9 | 50 | 41 | 4.80 | 10.4 | 1.9 | 4.0 | 3.0 | 4.9 | 8.9 | 455 | 0 |
| | 1 | 9 | 50 | 41 | 4.67 | 11.6 | 2.4 | 4.0 | 3.1 | 5.5 | 9.5 | 694 | 0 |
| | x2 | 9 | 51 | 42 | 4.42 | 11.1 | | | | | | 796 | 28 |
| | 1 | 9 | 51 | 42 | 4.75 | 8.6 | | | | | | 767 | 8 |
| | 1 | 9 | 54 | 45 | 4.40 | 11.2 | 2.2 | 2.5 | 2.4 | 4.4 | 7.1 | 745 | 19 |
| | 1 | 9 | 54 | 45 | 4.47 | 8.5 | 1.8 | 1.3 | 1.9 | 3.8 | 5.1 | 705 | 11 |
| YUSAZ A/1 X YUSOL/1 Maturity reached between cycle 35 and 42 | 1 | 14 | 37 | 25 | 5.22 | 7.1 | 2.5 | 0.0 | 2.6 | 5.1 | 5.1 | 284 | 406 |
| | x2 | 10 | 37 | 27 | 4.38 | 5.9 | 2.1 | 0.0 | 1.8 | 6.7 | 3.9 | 513 | 146 |
| | x2 | 9 | 37 | 28 | 4.67 | 5.5 | 2.0 | 0.0 | 2.7 | 4.7 | 4.7 | 530 | 93 |
| | x2 | 9 | 37 | 28 | 4.37 | 6.2 | 2.1 | 0.0 | 2.0 | 4.0 | 4.1 | 695 | 104 |
| | 1 | 19 | 47 | 28 | 5.23 | 5.8 | 1.9 | 0.6 | 3.1 | 5.0 | 5.6 | 410 | 0 |
| | 1 | 9 | 37 | 28 | 4.65 | 7.2 | 2.8 | 0.0 | 3.4 | 6.2 | 6.2 | 594 | 22 |
| | x2 | 9 | 40 | 31 | 4.66 | 7.0 | 2.0 | 0.4 | 2.8 | 4.8 | 5.2 | 490 | 12 |
| | 1 | 9 | 40 | 31 | 4.50 | 7.4 | 2.3 | 0.1 | 2.8 | 5.1 | 5.2 | 635 | 36 |
| | x2 | 9 | 40 | 31 | 4.32 | 5.9 | 2.2 | 0.0 | 2.1 | 4.0 | 4.3 | 495 | 102 |
| | x2 | 9 | 44 | 35 | 4.39 | 7.3 | 2.7 | 0.3 | 2.4 | 4.2 | 5.4 | 579 | 55 |
| | 1 | 9 | 44 | 35 | 4.62 | 9.2 | 2.5 | 1.2 | 3.0 | 5.5 | 6.7 | 689 | 0 |
| | 1 | 9 | 44 | 35 | 4.39 | 8.4 | 3.0 | 0.0 | 3.5 | 6.7 | 6.6 | 685 | 55 |
| | x2 | 9 | 44 | 35 | 4.41 | 8.8 | 3.0 | 0.3 | 3.0 | 5.4 | 6.3 | 702 | 27 |
| | 1 | 9 | 44 | 35 | 4.77 | 9.6 | 2.7 | 1.6 | 3.4 | 6.2 | 7.8 | 736 | 4 |
| | x2 | 9 | 44 | 35 | 5.85 | 8.0 | 1.9 | 3.1 | 3.4 | 5.3 | 8.4 | 387 | 0 |
| | x2 | 9 | 47 | 38 | 4.46 | 8.9 | 3.1 | 0.3 | 3.6 | 6.9 | 7.1 | 653 | 37 |
| | x2 | 9 | 47 | 38 | 4.85 | 11.4 | 3.9 | 2.4 | 4.7 | 8.6 | 11.0 | 776 | 17 |

TABLE 17-continued

|  |  |  |  |  |  |  |  |  |  |  |  |  |
|---|---|---|---|---|---|---|---|---|---|---|---|---|
|  | 1 | 9 | 47 | 38 | 6.46 | 9.4 | 1.3 | 3.6 | 2.8 | 4.1 | 7.8 | 274 | 0 |
|  | x2 | 9 | 47 | 38 | 4.75 | 9.2 | 2.8 | 1.4 | 3.1 | 5.9 | 7.3 | 525 | 0 |
|  | 1 | 9 | 51 | 42 | 4.87 | 12.4 | 2.8 | 4.3 | 3.1 | 5.9 | 10.2 | 696 | 19 |
|  | x2 | 9 | 51 | 42 | 4.45 | 11.4 | 2.6 | 3.9 | 3.2 | 5.8 | 9.7 | 678 | 11 |
|  | x2 | 9 | 51 | 42 | 4.57 | 14.4 |  |  |  |  |  | 791 | 47 |
|  | x2 | 9 | 51 | 42 | 4.41 | 11.6 | 2.7 | 3.0 | 2.6 | 5.1 | 8.3 | 730 | 52 |
|  | x2 | 9 | 51 | 42 | 4.73 | 13.8 | 2.5 | 5.3 | 3.5 | 6.0 | 11.3 | 679 | 0 |
|  | 1 | 10 | 53 | 43 | 6.24 | 11.0 |  |  |  |  |  | 410 | 47 |
|  | x2 | 10 | 53 | 43 | 6.18 | 10.5 |  |  |  |  |  | 350 | 48 |
|  | 1 | 9 | 54 | 45 | 4.58 | 13.5 | 2.7 | 4.8 | 2.8 | 4.8 | 10.4 | 780 | 62 |
|  | 1x | 9 | 54 | 45 | 4.54 | 13.2 | 2.5 | 4.2 | 2.3 | 4.4 | 9.0 | 751 | 34 |
| YUSAZ A/2 | x2 | 10 | 37 | 27 | 4.55 | 7.0 | 2.7 | 0.0 | 3.1 | 5.7 | 5.8 | 543 | 24 |
| X YUSOL/3 | x2 | 10 | 37 | 27 | 4.52 | 7.6 | 2.8 | 0.0 | 3.1 | 6.0 | 5.9 | 640 | 64 |
| Maturity | 1 | 9 | 37 | 28 | 5.46 | 8.3 | 2.2 | 1.1 | 2.9 | 4.9 | 6.2 | 457 | 166 |
| reached between | x2 | 9 | 37 | 28 | 4.40 | 6.1 | 2.5 | 0.0 | 2.5 | 4.4 | 5.0 | 630 | 64 |
| cycle 34 to 38 | 1 | 9 | 37 | 28 | 4.67 | 9.4 | 2.9 | 2.5 | 4.1 | 7.0 | 9.5 | 618 | 30 |
|  | 1 | 10 | 40 | 30 | 4.71 | 9.5 | 3.1 | 1.3 | 3.3 | 6.4 | 7.7 | 610 | 54 |
|  | x2 | 9 | 40 | 31 | 4.51 | 6.6 | 2.4 | 0.0 | 2.7 | 5.2 | 5.1 | 460 | 64 |
|  | x2 | 9 | 40 | 31 | 4.62 | 7.7 | 3.0 | 0.0 | 3.2 | 6.1 | 6.1 | 569 | 50 |
|  | x2 | 9 | 40 | 31 | 4.58 | 7.6 | 2.7 | 0.0 | 3.2 | 5.2 | 6.0 | 655 | 41 |
|  | x2 | 9 | 40 | 31 | 4.48 | 8.3 | 2.9 | 0.0 | 3.4 | 2.6 | 6.3 | 721 | 48 |
|  | 1 | 10 | 44 | 34 | 4.76 | 11.2 | 3.4 | 1.0 | 4.0 | 7.2 | 8.5 | 844 | 74 |
|  | 1 | 10 | 44 | 34 | 4.69 | 13.1 | 3.1 | 3.1 | 3.9 | 9.7 | 10.0 | 825 | 90 |
|  | 1 | 17 | 51 | 34 | 4.72 | 10.1 |  |  |  |  |  | 612 | 22 |
|  | x2 | 10 | 44 | 34 | 4.48 | 12.1 | 3.4 | 2.0 | 4.0 | 6.7 | 9.4 | 683 | 64 |
|  | 1 | 9 | 44 | 35 | 4.66 | 13.0 | 3.3 | 4.2 | 3.5 | 6.8 | 11.0 | 733 | 42 |
|  | 1 | 9 | 47 | 38 | 5.22 | 14.4 | 2.6 | 5.9 | 3.0 | 5.6 | 11.4 | 514 | 87 |
|  | 1 | 9 | 47 | 38 | 4.50 | 13.2 | 3.1 | 4.1 | 3.1 | 5.8 | 10.3 | 899 | 80 |
|  | x2 | 9 | 47 | 38 | 4.89 | 12.4 | 2.2 | 4.1 | 3.2 | 6.7 | 9.5 | 696 | 21 |
|  | 1 | 9 | 47 | 38 | 4.57 | 14.2 | 3.3 | 4.3 | 3.3 | 6.2 | 10.9 | 725 | 66 |
|  | 1 | 9 | 47 | 38 | 4.66 | 15.2 | 2.8 | 5.7 | 2.9 | 4.8 | 11.4 | 774 | 141 |
|  | x2 | 10 | 51 | 41 | 4.67 | 15.2 |  |  |  |  |  | 818 | 44 |
|  | x2 | 9 | 51 | 42 | 4.74 | 13.6 |  |  |  |  |  | 754 | 65 |
|  | 1 | 9 | 51 | 42 | 4.97 | 15.4 | 2.1 | 7.0 | 2.6 | 4.7 | 11.7 | 507 | 1 |
|  | 1 | 9 | 51 | 42 | 5.60 | 15.2 | 2.0 | 8.6 | 2.3 | 4.3 | 12.9 | 462 | 97 |
|  | 1 | 11 | 54 | 43 | 4.94 | 15.8 | 2.9 | 6.0 | 2.8 | 8.1 | 11.7 | 680 | 66 |
|  | x2 | 9 | 53 | 44 | 4.93 | 15.1 |  |  |  |  |  | 881 | 221 |
|  | x2 | 9 | 54 | 45 | 4.80 | 15.3 | 2.3 | 7.4 | 2.7 | 5.1 | 12.4 | 831 | 103 |
|  | x2 | 9 | 54 | 45 | 4.53 | 14.1 | 2.7 | 5.2 | 2.8 | 5.2 | 10.8 | 876 | 64 |
|  | 1 | 9 | 54 | 45 | 5.00 | 15.8 | 2.8 | 6.3 | 2.5 | 4.8 | 11.6 | 641 | 188 |

Example 16

Post Harvest Evolution of Fruit Characteristics

A. Fruits of plants of trial SP030F (see Tables 6 and 7C) were harvested and stored for 1 week at 12° C. followed by 3 days at 20° C. or for 6 weeks at 12° C. followed by 2 days at 20° C. The characteristics of the fruits were measured after storage and are shown in Table 18.

B. Plants were grown as for the plants in Table 14 above. Fruits were harvested and stored for 1 week at 12° C. followed by 3 days at 20° C. The characteristics of the fruits were measured after storage and are shown in Table 19.

TABLE 18

|  | Post harvest protocol | Hv | FRT Nr | Brix | pH | Glu g/100 g | Suc g/100 g | Fru g/100 g | Hex g/100 g | Total Sugar | Citric mg/100 g | Malic mg/100 g |
|---|---|---|---|---|---|---|---|---|---|---|---|---|
| Millenium | 1 w 12° + 3 d 20° | Avg | 5 | 8.4 | 5.75 | 2.0 | 2.3 | 2.2 | 4.2 | 6.4 | 441 | −8 |
|  |  | Stdev |  | 0.3 | 0.05 | 0.1 | 0.2 | 0.0 | 0.1 | 0.2 | 25 | 4 |
|  | 6 w 12° + 2 d 20° | Avg | 2 | 10.1 | 5.86 | 1.5 | 3.9 | 2.2 | 3.7 | 7.6 | 487 |  |
|  |  | Stdev |  | 0.6 | 0.03 | 0.3 | 0.9 | 0.2 | 0.5 | 0.4 | 4 |  |
| YUSOL/1&2 X SOLAZ/1 | 1 w 12° + 3 d 20° | Avg | 4 | 12.0 | 4.71 | 1.0 | 6.7 | 2.1 | 3.1 | 9.8 | 802 | −1 |
|  |  | Stdev |  | 0.7 | 0.05 | 0.1 | 0.7 | 0.1 | 0.2 | 0.7 | 33 | 6 |
|  | 6 w 12° + 2 d 20° | Avg | 2 | 13.2 | 4.77 | 0.5 | 8.1 | 1.8 | 2.3 | 10.4 | 808 |  |
|  |  | Stdev |  | 0.5 | 0.07 | 0.1 | 0.6 | 0.0 | 0.1 | 0.5 | 36 |  |
| YUSOL/3 X SOLAZ/1 | 6 w 12° + 2 d 20° | Avg | 4 | 11.9 | 4.89 | 1.1 | 6.2 | 1.9 | 3.0 | 9.2 | 638 |  |
|  |  | Stdev |  | 0.9 | 0.07 | 0.4 | 1.6 | 0.3 | 0.7 | 1.1 | 72 |  |
| YUSOL/1 X SOLAZ/2 | 1 w 12° + 3 d 20° | Avg | 9 | 9.5 | 4.46 | 1.0 | 4.5 | 1.9 | 2.9 | 7.4 | 773 | −5 |
|  |  | Stdev |  | 1.4 | 0.12 | 0.2 | 1.5 | 0.2 | 0.4 | 1.2 | 85 | 5 |
|  | 6 w 12° + 2 d 20° | Avg | 4 | 9.5 | 4.65 | 1.1 | 3.7 | 2.0 | 3.1 | 6.7 | 669 |  |
|  |  | Stdev |  | 1.4 | 0.17 | 0.2 | 1.4 | 0.3 | 0.5 | 1.0 | 70 |  |
| YUSOL/2 X SOLAZ/2 | 1 w 12° + 3 d 20° | Avg | 5 | 10.1 | 4.53 | 1.1 | 4.9 | 2.1 | 3.2 | 8.2 | 789 | 3 |
|  |  | Stdev |  | 2.3 | 0.13 | 0.2 | 2.3 | 0.2 | 0.3 | 2.1 | 95 |  |
|  | 6 w 12° + 2 d 20° | Avg | 2 | 10.6 | 4.70 | 1.1 | 5.5 | 2.0 | 3.1 | 8.6 | 697 |  |
|  |  | Stdev |  | 0.7 | 0.02 | 0.1 | 0.6 | 0.1 | 0.2 | 0.4 | 51 |  |

TABLE 18-continued

| | Post harvest protocol | Hv | FRT Nr | Brix | pH | Glu g/100 g | Suc g/100 g | Fru g/100 g | Hex g/100 g | Total Sugar | Citric mg/100 g | Malic mg/100 g |
|---|---|---|---|---|---|---|---|---|---|---|---|---|
| YUSOL/3 X SOLAZ/2 | 1 w 12° + 3 d 20° | Avg | 12 | 10.4 | 4.50 | 0.9 | 5.8 | 1.8 | 2.7 | 8.4 | 777 | −4 |
| | | Stdev | | 0.8 | 0.09 | 0.2 | 0.9 | 0.1 | 0.3 | 0.8 | 37 | 6 |
| | 6 w 12° + 2 d 20° | Avg | 6 | 11.0 | 4.85 | 0.6 | 6.2 | 1.5 | 2.1 | 8.3 | 656 | |
| | | Stdev | | 0.8 | 0.14 | 0.3 | 1.1 | 0.3 | 0.6 | 0.7 | 46 | |

TABLE 19

| | FRT Nr | Brix | pH | GLU g/100 g | SUC g/100 g | FRU g/100 g | Tot sug g/100 g | Citric Ac mg/100 g | Malic Ac mg/100 g | ratio Citric Ac/Malic Ac |
|---|---|---|---|---|---|---|---|---|---|---|
| SOLAZ/2 X YUSOL/3 | 51 | 13.1 | 4.75 | 1.4 | 7.2 | 2.0 | 10.6 | 771 | 23 | 35 |
| SOLAZ/1 X YUSOL/1 | 51 | 13.8 | 4.71 | 1.8 | 7.9 | 2.3 | 12.0 | 778 | 21 | 53 |
| YUSOL/1 X SOLAZ/1 basic | 51 | 13.4 | 6.14 | 1.4 | 8.0 | 2.3 | 11.7 | 354 | 14 | 31 |
| MEHARY | 10 | 14.8 | 6.51 | 0.5 | 10.4 | 1.3 | 12.2 | 289 | 73 | 4 |
| Female MEHARI X L53 AZ/A | 59 | 12.4 | 5.45 | 0.8 | 7.4 | 1.4 | 9.7 | 491 | 211 | 2 |
| TD x L53AZ/A | 49 | 13.9 | 5.16 | 0.6 | 9.0 | 1.3 | 10.9 | 579 | 69 | 11 |

What is claimed is:

1. A method of increasing the citric acid content of a fruit of a first *C. melo* plant comprising:

a) obtaining a first *C. melo* plant;

b) crossing said first *C. melo* plant with a second *C. melo* plant, wherein said second *C. melo* plant is a plant of line IND-35, representative seed of which is deposited under Accession number NCIMB 41202; and c) selecting a progeny *C. melo* plant comprising in its genome the molecular markers NE0585 and NE1746, and producing a fruit having:

i) increased citric acid content and lower pH, when compared to a fruit of said first *C. melo* plant grown under similar conditions, and ii) a ratio of citric acid to malic acid that is greater than 5, wherein selecting comprises detecting at least one amplified DNA fragment of a length of 228 bp, 230 bp, 232 bp, and/or 253 bp when amplifying in the molecular marker NEO585 with an amplification primer pair of SEQ ID NO:3 and SEQ ID NO:4, or 121 bp, 124 bp, and/or 127 bp when amplifying the molecular marker NE1746 with an amplification primer pair of SEQ ID NO:5 and SEQ ID NO:6.

* * * * *

UNITED STATES PATENT AND TRADEMARK OFFICE
CERTIFICATE OF CORRECTION

PATENT NO. : 8,829,265 B2  
APPLICATION NO. : 12/549728  
DATED : September 9, 2014  
INVENTOR(S) : Alvarez Casanueva et al.

Page 1 of 1

It is certified that error appears in the above-identified patent and that said Letters Patent is hereby corrected as shown below:

In the Claims:

Column 56, Claim 1, Line 30: Please correct "when amplifying in the"
to read -- when amplifying the --

Signed and Sealed this
Tenth Day of February, 2015

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
aagcacacca ccacccgtaa                                                   20

<210> SEQ ID NO 2
<211> LENGTH: 21
<212> TYPE: DNA
<213> ORGANISM: Artificial Sequence
<220> FEATURE:
<223> OTHER INFORMATION: oligonucleotide

<400> SEQUENCE: 2
gtgaatggta tgttatcctt g                                                 21

<210> SEQ ID NO 3
<211> LENGTH: 19
<212> TYPE: DNA
<213> ORGANISM: Artificial Sequence
<220> FEATURE:
<223> OTHER INFORMATION: oligonucleotide

<400> SEQUENCE: 3
gtatcatgtc ggagaaacg                                                    19

<210> SEQ ID NO 4
<211> LENGTH: 19
<212> TYPE: DNA
<213> ORGANISM: Artificial Sequence
<220> FEATURE:
<223> OTHER INFORMATION: oligonucleotide

<400> SEQUENCE: 4
cctttatccc cacttttc                                                     19
```

```
<210> SEQ ID NO 5
<211> LENGTH: 19
<212> TYPE: DNA
<213> ORGANISM: Artificial Sequence
<220> FEATURE:
<223> OTHER INFORMATION: oligonucleotide

<400> SEQUENCE: 5
ttctccgatg tgtcctctc                                                19

<210> SEQ ID NO 6
<211> LENGTH: 19
<212> TYPE: DNA
<213> ORGANISM: Artificial Sequence
<220> FEATURE:
<223> OTHER INFORMATION: oligonucleotide

<400> SEQUENCE: 6
gtcgcttgga atatatcgg                                                19
```